US012324610B2

(12) United States Patent
Martin et al.

(10) Patent No.: US 12,324,610 B2
(45) Date of Patent: Jun. 10, 2025

(54) LEVER REDUCER

(71) Applicant: Spinal Elements, Inc., Carlsbad, CA (US)

(72) Inventors: Gregory Martin, Carlsbad, CA (US); Jason Blain, Encinitas, CA (US); Taylor Semingson, San Diego, CA (US); Peter Bono, Bingham Farms, MI (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 17/723,932

(22) Filed: Apr. 19, 2022

(65) Prior Publication Data

US 2022/0346845 A1 Nov. 3, 2022

Related U.S. Application Data

(60) Provisional application No. 63/180,931, filed on Apr. 28, 2021.

(51) Int. Cl.
*A61B 17/70* (2006.01)
(52) U.S. Cl.
CPC ................. *A61B 17/7077* (2013.01)
(58) Field of Classification Search
CPC ............. A61B 17/7077; A61B 17/708; A61B 17/7085; A61B 17/7086; A61B 17/7079
USPC ................. 606/250–279, 86, 53–59
See application file for complete search history.

(56) References Cited

U.S. PATENT DOCUMENTS

| 2,102,602 A | 12/1937 | Nash |
| 3,604,487 A | 9/1971 | Gilbert |
| 4,411,259 A | 10/1983 | Drummond |
| 5,020,519 A | 6/1991 | Hayes et al. |

(Continued)

FOREIGN PATENT DOCUMENTS

| DE | 42 38 339 | 5/1994 |
| EP | 2 098 178 | 12/2011 |

(Continued)

OTHER PUBLICATIONS

U.S. Appl. No. 60/422,455, filed Oct. 30, 2002, Landry et al.

(Continued)

*Primary Examiner* — Eduardo C Robert
*Assistant Examiner* — Tara Rose E Carter
(74) *Attorney, Agent, or Firm* — Knobbe, Martens, Olson & Bear, LLP

(57) ABSTRACT

Embodiments of a lever reducer and methods of using a lever reducer are provided. In some embodiments, the lever reducer system includes a first tower, a second tower, and a lever reducer configured to couple to the first tower and the second tower. The lever reducer can include a fulcrum configured to be coupled to the first tower and a swivel configured to be coupled to the second tower. The lever reducer is configured to vertically lift the second tower. The method can include coupling a first tower to a first vertebra, as well as coupling a second tower to a second vertebra. The method can include coupling a lever reducer to the first tower and the second tower by coupling a fulcrum to the first tower and a swivel to the second tower. The method can include applying a force to the lever reducer to vertically lift the second tower.

22 Claims, 17 Drawing Sheets

(56) References Cited

U.S. PATENT DOCUMENTS

| | | |
|---|---|---|
| 5,364,397 A | 11/1994 | Hayes et al. |
| 5,449,361 A | 9/1995 | Preissman |
| 5,720,751 A | 2/1998 | Jackson |
| 5,782,830 A | 7/1998 | Farris |
| 5,810,378 A | 9/1998 | Brinkley |
| 5,810,878 A | 9/1998 | Burel et al. |
| 5,910,141 A | 6/1999 | Morrison et al. |
| 6,036,692 A | 3/2000 | Burel et al. |
| 6,342,057 B1 | 1/2002 | Brace et al. |
| 6,440,133 B1 | 8/2002 | Beale et al. |
| 6,530,929 B1 | 3/2003 | Justis et al. |
| 6,565,568 B1* | 5/2003 | Rogozinski ........ A61B 17/7077 606/279 |
| 6,660,006 B2 | 12/2003 | Markworth et al. |
| 6,660,022 B1 | 12/2003 | Li et al. |
| 6,736,829 B1 | 5/2004 | Li et al. |
| 6,790,209 B2 | 9/2004 | Beale |
| 6,830,574 B2 | 12/2004 | Heckele et al. |
| 6,916,323 B2 | 7/2005 | Kitchens |
| 7,004,947 B2 | 2/2006 | Shluzas et al. |
| 7,008,422 B2 | 3/2006 | Foley et al. |
| 7,011,660 B2 | 3/2006 | Sherman et al. |
| 7,041,120 B2 | 5/2006 | Li et al. |
| 7,083,612 B2 | 8/2006 | Littrup et al. |
| 7,160,300 B2 | 1/2007 | Jackson |
| 7,179,261 B2 | 2/2007 | Sicvol et al. |
| 7,188,626 B2 | 3/2007 | Foley et al. |
| 7,250,052 B2 | 7/2007 | Landry et al. |
| 7,306,603 B2 | 12/2007 | Boehm, Jr. et al. |
| 7,322,979 B2 | 1/2008 | Crandall et al. |
| 7,341,594 B2 | 3/2008 | Shluzas et al. |
| 7,431,731 B2 | 10/2008 | Kitchens |
| 7,473,267 B2 | 1/2009 | Nguyen et al. |
| 7,476,240 B2 | 1/2009 | Raymond et al. |
| 7,491,218 B2 | 2/2009 | Landry et al. |
| 7,520,879 B2 | 4/2009 | Justis et al. |
| 7,527,638 B2 | 5/2009 | Anderson et al. |
| 7,563,264 B2 | 7/2009 | Landry et al. |
| 7,572,276 B2 | 8/2009 | Lim et al. |
| 7,588,575 B2 | 9/2009 | Colleran et al. |
| 7,588,588 B2 | 9/2009 | Spitler et al. |
| 7,597,694 B2 | 10/2009 | Lim et al. |
| 7,618,424 B2 | 11/2009 | Wilcox et al. |
| 7,618,442 B2 | 11/2009 | Spitler et al. |
| 7,618,444 B2 | 11/2009 | Shluzas |
| 7,637,914 B2 | 12/2009 | Stern |
| 7,648,506 B2 | 1/2010 | McCord et al. |
| 7,648,507 B2 | 1/2010 | Techiera et al. |
| 7,650,919 B2 | 1/2010 | Rhyne et al. |
| 7,666,189 B2 | 2/2010 | Gerber et al. |
| 7,686,809 B2 | 3/2010 | Triplett et al. |
| 7,691,132 B2 | 4/2010 | Landry et al. |
| 7,695,475 B2 | 4/2010 | Justis et al. |
| 7,713,274 B2 | 5/2010 | Shluzas et al. |
| 7,717,944 B2 | 5/2010 | Foley et al. |
| 7,749,232 B2 | 7/2010 | Salerni |
| 7,758,617 B2 | 7/2010 | Lott et al. |
| 7,763,030 B2 | 7/2010 | Blau et al. |
| 7,763,055 B2 | 7/2010 | Foley |
| 7,776,040 B2 | 8/2010 | Markworth et al. |
| 7,794,479 B2 | 9/2010 | Aferzon |
| 7,815,650 B2 | 10/2010 | Shluzas et al. |
| 7,824,410 B2 | 11/2010 | Simonson et al. |
| 7,862,595 B2 | 1/2011 | Foley et al. |
| 7,871,413 B2 | 1/2011 | Park et al. |
| 7,871,424 B2 | 1/2011 | Abdelgany |
| 7,875,031 B2 | 1/2011 | Chin et al. |
| 7,905,907 B2 | 3/2011 | Spitler et al. |
| 7,909,830 B2 | 3/2011 | Frigg et al. |
| 7,914,558 B2 | 3/2011 | Landry et al. |
| 7,918,878 B2 | 4/2011 | Songer et al. |
| 7,922,727 B2 | 4/2011 | Songer et al. |
| 7,922,731 B2 | 4/2011 | Schumacher et al. |
| 7,951,152 B2 | 5/2011 | Marino |
| 7,967,826 B2 | 6/2011 | Colleran et al. |
| 7,976,546 B2 | 7/2011 | Geist et al. |
| 7,998,144 B2 | 8/2011 | Schumacher et al. |
| 8,002,798 B2 | 8/2011 | Chin et al. |
| 8,034,084 B2 | 10/2011 | Landry et al. |
| 8,043,343 B2 | 10/2011 | Miller et al. |
| 8,048,129 B2 | 11/2011 | Forton et al. |
| 8,070,751 B2 | 12/2011 | Justis et al. |
| 8,075,592 B2 | 12/2011 | Landry et al. |
| 8,097,027 B2 | 1/2012 | Lim et al. |
| 8,105,361 B2 | 1/2012 | Anderson et al. |
| 8,246,624 B2 | 8/2012 | Forton et al. |
| 8,308,728 B2 | 11/2012 | Lott et al. |
| 8,343,160 B2 | 1/2013 | Techiera et al. |
| 8,394,109 B2 | 3/2013 | Hutton et al. |
| 8,439,924 B1 | 5/2013 | McBride et al. |
| 8,469,960 B2 | 6/2013 | Hutton et al. |
| 8,491,590 B2 | 7/2013 | Stad et al. |
| 8,603,094 B2 | 12/2013 | Walker et al. |
| RE44,813 E | 3/2014 | Beale et al. |
| 8,734,490 B2 | 5/2014 | Anderson et al. |
| 8,821,502 B2 | 9/2014 | Gleeson et al. |
| 8,864,767 B2 | 10/2014 | Blain et al. |
| 8,906,034 B2 | 12/2014 | Gleeson et al. |
| 8,915,925 B2 | 12/2014 | Butters et al. |
| 8,961,524 B2 | 2/2015 | Foley et al. |
| 9,060,825 B2 | 6/2015 | Hutton et al. |
| 9,101,401 B2 | 8/2015 | Dalton et al. |
| 9,101,414 B2 | 8/2015 | King et al. |
| 9,131,967 B2 | 9/2015 | Stad et al. |
| 9,561,062 B2 | 2/2017 | Hayes et al. |
| 9,579,140 B2 | 2/2017 | Jones et al. |
| 9,833,268 B2 | 12/2017 | Walker |
| 9,974,577 B1 | 5/2018 | Smith et al. |
| 10,070,900 B2 | 9/2018 | Hayes et al. |
| 10,085,778 B2 | 10/2018 | Semingson et al. |
| 10,194,960 B1 | 2/2019 | Hammann et al. |
| 10,682,166 B2 | 6/2020 | Smith et al. |
| 10,856,915 B2 | 12/2020 | Hayes |
| 11,006,983 B2 | 5/2021 | Hammann et al. |
| 2003/0225408 A1 | 12/2003 | Nichols et al. |
| 2004/0172022 A1 | 9/2004 | Landry et al. |
| 2005/0090824 A1 | 4/2005 | Shluzas et al. |
| 2005/0192571 A1 | 9/2005 | Abdelgany |
| 2005/0192579 A1 | 9/2005 | Jackson et al. |
| 2005/0240275 A1 | 10/2005 | Chappuis |
| 2006/0079909 A1 | 4/2006 | Runco et al. |
| 2006/0142761 A1 | 6/2006 | Landry et al. |
| 2006/0200128 A1 | 9/2006 | Mueller |
| 2006/0229614 A1 | 10/2006 | Foley et al. |
| 2007/0005146 A1 | 1/2007 | Heyligers et al. |
| 2007/0016194 A1 | 1/2007 | Shaolian et al. |
| 2007/0173831 A1 | 7/2007 | Abdou |
| 2007/0270867 A1* | 11/2007 | Miller ................ A61B 17/7088 606/86 R |
| 2007/0270869 A1 | 11/2007 | Young et al. |
| 2008/0039839 A1 | 2/2008 | Songer et al. |
| 2008/0077138 A1 | 3/2008 | Cohen et al. |
| 2008/0077139 A1 | 3/2008 | Landry et al. |
| 2008/0119852 A1* | 5/2008 | Dalton ............... A61B 17/7091 606/86 R |
| 2008/0161857 A1 | 7/2008 | Hestad et al. |
| 2008/0228228 A1 | 9/2008 | Hestad et al. |
| 2008/0243190 A1 | 10/2008 | Dziedzic et al. |
| 2008/0249531 A1 | 10/2008 | Patterson |
| 2008/0269805 A1 | 10/2008 | Dekutoski et al. |
| 2008/0312703 A1 | 12/2008 | Hestad et al. |
| 2009/0012563 A1 | 1/2009 | Alleyne et al. |
| 2009/0062857 A1 | 3/2009 | Ramsay et al. |
| 2009/0082809 A1 | 3/2009 | Nguyen et al. |
| 2009/0105774 A1 | 4/2009 | Jones et al. |
| 2009/0125032 A1 | 5/2009 | Gutierrez et al. |
| 2009/0143828 A1 | 6/2009 | Stad et al. |
| 2009/0171391 A1 | 7/2009 | Hutton et al. |
| 2009/0182382 A1 | 7/2009 | Justis et al. |
| 2009/0312797 A1 | 12/2009 | Lim et al. |
| 2009/0326586 A1 | 12/2009 | Duarte |
| 2010/0030283 A1* | 2/2010 | King ................ A61B 17/7082 606/104 |
| 2010/0094359 A1 | 4/2010 | Techiera et al. |

(56) References Cited

U.S. PATENT DOCUMENTS

| | | |
|---|---|---|
| 2010/0222828 A1 | 9/2010 | Stad et al. |
| 2010/0228303 A1 | 9/2010 | Salerni |
| 2010/0249856 A1 | 9/2010 | Iott et al. |
| 2010/0331901 A1 | 12/2010 | Iott et al. |
| 2011/0022088 A1 | 1/2011 | Forton et al. |
| 2011/0071571 A1 | 3/2011 | Abdelgany |
| 2011/0152940 A1 | 6/2011 | Frigg et al. |
| 2011/0152942 A1 | 6/2011 | Oh et al. |
| 2011/0184464 A1 | 7/2011 | Fiorella |
| 2011/0196426 A1 | 8/2011 | Peukert et al. |
| 2011/0218581 A1* | 9/2011 | Justis ............... A61B 17/708 606/86 R |
| 2011/0238117 A1 | 9/2011 | Geist et al. |
| 2012/0031792 A1* | 2/2012 | Petit ............... A61B 50/30 606/86 A |
| 2012/0283786 A1 | 11/2012 | Rezach et al. |
| 2013/0245692 A1* | 9/2013 | Hayes ............... A61B 17/025 606/279 |
| 2014/0148865 A1 | 5/2014 | Hennard et al. |
| 2015/0066042 A1 | 3/2015 | Cummins et al. |
| 2015/0148853 A1* | 5/2015 | Hawkes ............. A61B 17/7083 606/86 A |
| 2016/0262807 A1* | 9/2016 | Benson ............. A61B 17/7077 |
| 2017/0112539 A1* | 4/2017 | Hayes ............... A61B 17/708 |
| 2020/0113606 A1 | 4/2020 | Reitblat et al. |
| 2020/0261123 A1 | 8/2020 | Smith et al. |
| 2020/0297396 A1* | 9/2020 | Schmura ........... A61B 17/7086 |
| 2021/0077150 A1 | 3/2021 | Hayes |
| 2021/0346006 A1* | 11/2021 | Cestero ............. A61B 17/0206 |

FOREIGN PATENT DOCUMENTS

| | | |
|---|---|---|
| EP | 1 558 157 | 11/2012 |
| WO | WO 2005/023125 | 3/2005 |
| WO | WO 2016/077208 | 5/2016 |

OTHER PUBLICATIONS

U.S. Appl. No. 60/466,091, filed Apr. 28, 2003, Landry et al.

Foley et al., "Minimally Invasive Lumbar Fusion", Spine, 2003, vol. 28, No. 15S, pp. S26-S35.

Foley et al., "Percutaneous Pedicle Screw Fixation of the Lumbar Spine: Preliminary Clinical Results", Journal of Neurosurgery, Spine 1, 2002, vol. 97, pp. 7-12.

Khoo et al., "Minimally Invasive Percutaneous Posterior Lumbar Interbody Fusion", Neurosurgery, Nov. 2002, vol. 51, No. 2, pp. 166-181.

Kim et al., "Minimally Invasive Spine Instrumentation", Neurosurgery, Nov. 2002, vol. 51, No. 2, pp. 15-25.

McAfee et al., "Minimally Invasive Anterior Retroperitoneal Approach to the Lumbar Spine", Spine, 1998, vol. 23, No. 13, pp. 1476-1484.

Newton et al., "Thoracoscopic Multilevel Anterior Instrumented Fusion in a Goat Model", Spine, 2003, vol. 28, No. 14, pp. 1614-1620.

Onibokun et al., "Minimally Invasive Pedicle Screw Fixation", Operative Techniques in Neurosurgery, 2005, vol. 7, pp. 72-78.

Salerni, Anthony A., "Minimally Invasive Removal or Revision of Lumbar Spinal Fixation", The Spine Journal, 2004, vol. 4, No. 6, pp. 701-705.

Shamie et al., "Minimally Invasive Spinal Surgery", Operative Techniques in Orthopaedics, Jul. 2003, vol. 13, No. 3, pp. 202-206.

Teitelbaum et al., "New Percutaneously Inserted Spinal Fixation System", Spine, Mar. 15, 2004, vol. 29, No. 6, pp. 703-709.

Wang et al., "Minimally Invasive Lateral Mass Screws in the Treatment of Cervical Facet Dislocations: Technical Note", Neurosurgery, Feb. 2003, vol. 52, No. 2, pp. 444-448.

* cited by examiner

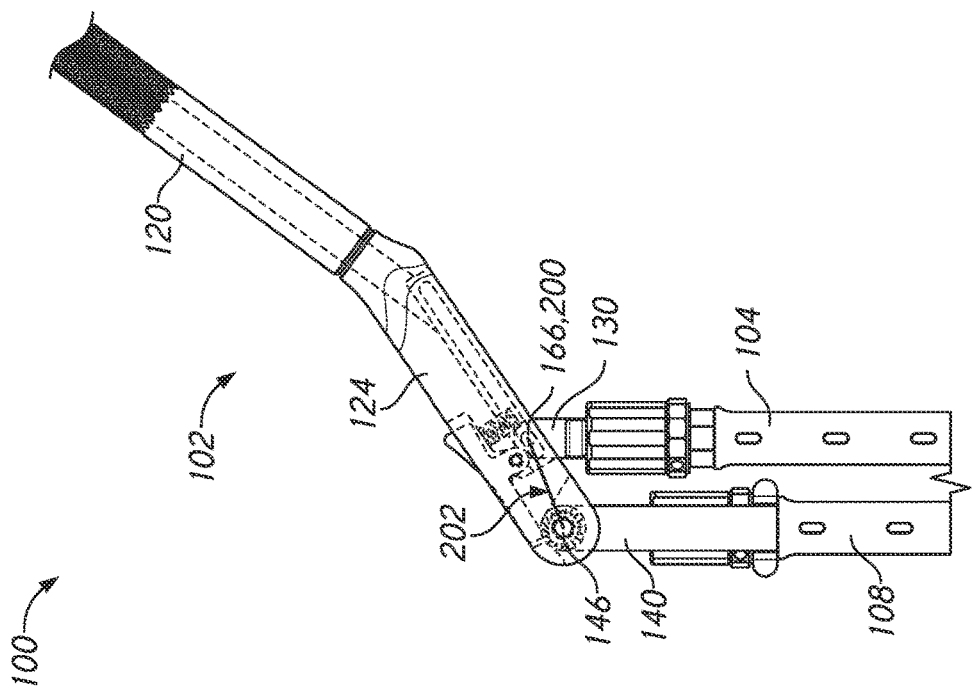
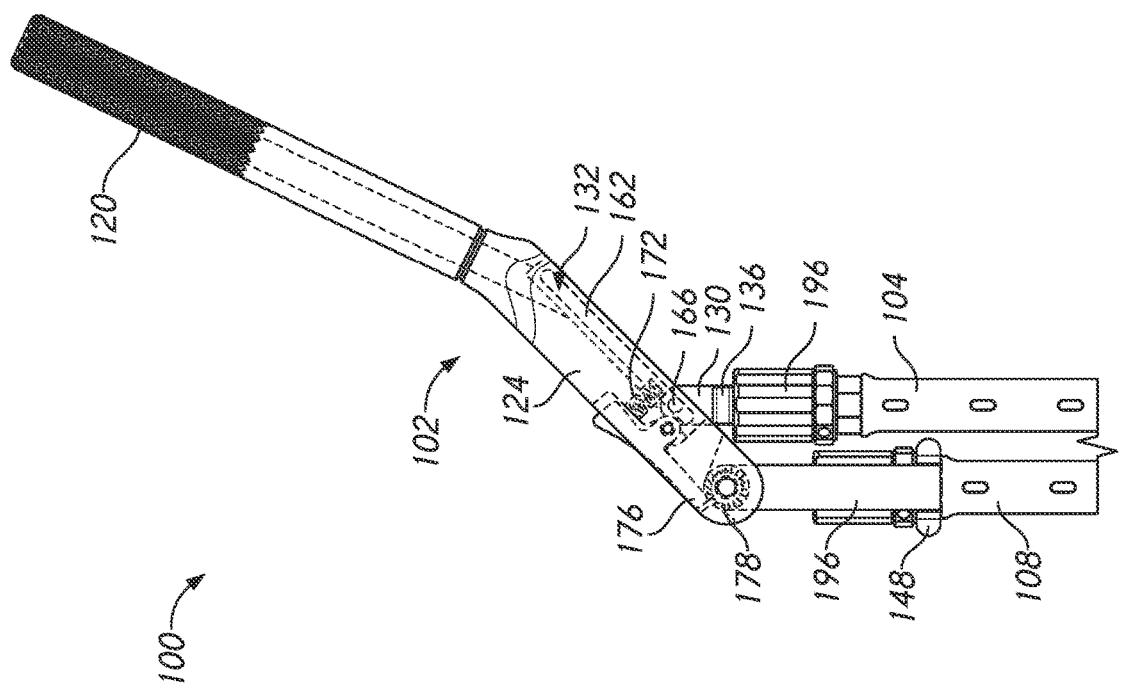

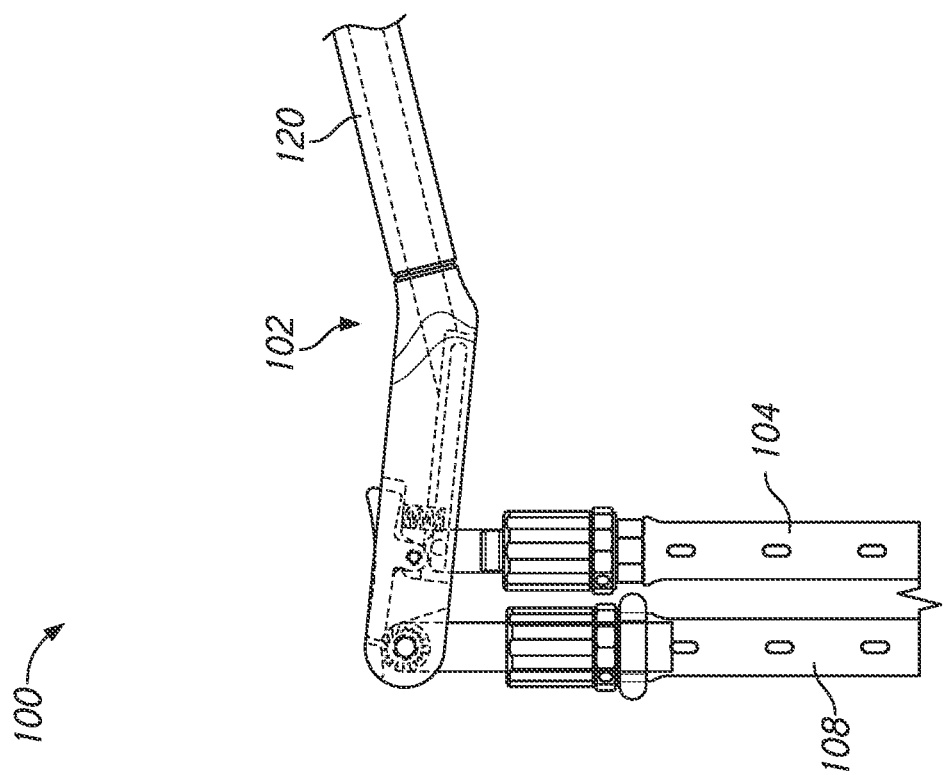
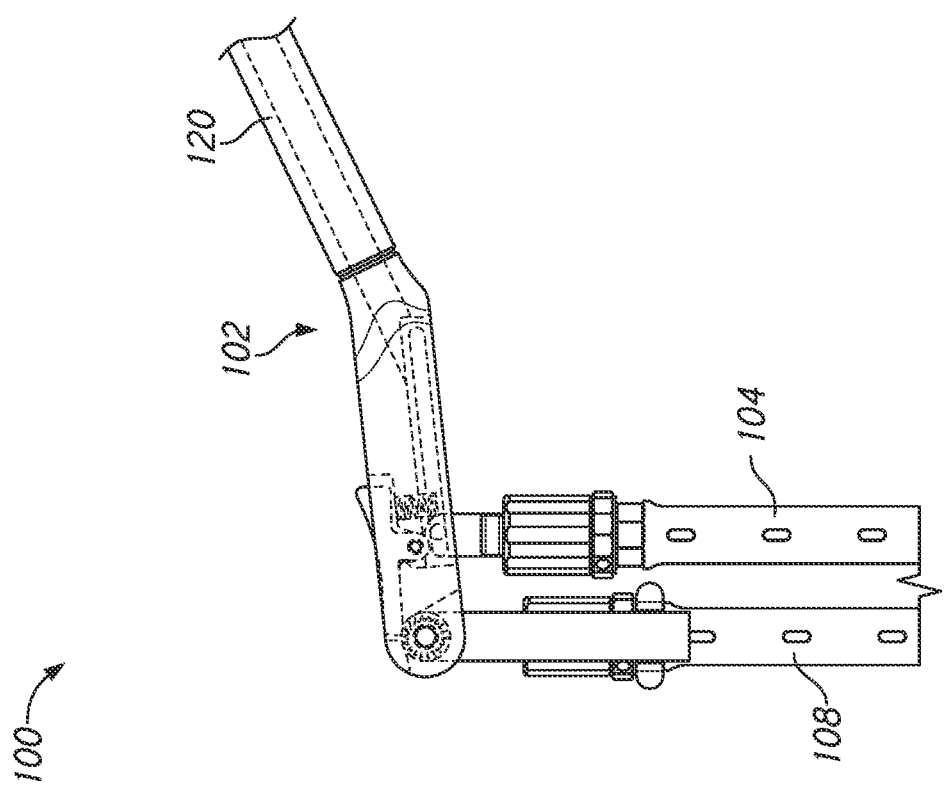

LEVER REDUCER

CROSS-REFERENCE TO RELATED APPLICATIONS

This application claims priority benefit to U.S. Provisional Patent Application No. 63/180,931, filed Apr. 28, 2021, the entirety of which is hereby incorporated by reference herein.

BACKGROUND

Field

The present disclosure relates to surgical instruments and methods for moving one component into an adjacent position to another component, in some cases moving a vertebra with an implanted fastener into an adjacent position to another vertebra with an implanted fastener.

Description of the Related Art

The vertebral column comprises a series of alternating vertebrae and fibrous discs that provide axial support and movement to the upper portions of the body. The vertebral column typically comprises thirty-three vertebrae, with seven cervical (C1-C7), twelve thoracic (T1-T12), five lumbar (L1-L5), five fused sacral (S1-S5) and four fused coccygeal vertebrae. Each vertebra includes an anterior body with a posterior arch. The posterior arch comprises two pedicles and two laminae that join posteriorly to form a spinous process. Projecting from each side of the posterior arch is a transverse, superior and inferior articular process. The facets of the superior and inferior articular processes form facet joints with the articular processes of the adjacent vertebrae.

The typical cervical vertebrae differ from the other vertebrae with relatively larger spinal canals, oval shaped vertebral bodies, bifid spinous processes and foramina in their transverse processes. These foramina transversaria contain the vertebral artery and vein. The first and second cervical vertebrae are also further differentiated from the other vertebrae. The first cervical vertebra lacks a vertebral body and instead contains an anterior tubercle. Its superior articular facets articulate with the occipital condyles of the skull and are oriented in a roughly parasagittal plane. The cranium is able to slide forward and backwards on this vertebra. The second cervical vertebra contains an odontoid process, or dens, which projects superiorly from its body. It articulates with the anterior tubercle of the atlas, forming a pivot joint. Side to side movements of the head occur at this joint. The seventh cervical vertebra is sometimes considered atypical since it lacks a bifid spinous process.

The typical lumbar vertebrae are distinguishable from the other vertebrae by the absence of foramina transversaria and the absence of facets on the surface of the vertebral body. The lumbar vertebral bodies are larger than the thoracic vertebral bodies and have thicker pedicles and laminae projecting posteriorly. The vertebral foramen is triangular in shape and larger than the foramina in the thoracic spine but smaller than the foramina in the cervical spine. The superior and inferior articular processes project superiorly and inferiorly from the pedicles, respectively. The sacrum is a large bone at the base of the spine formed by the fusion of the five sacral vertebrae (S1-S5).

In orthopedic surgery, and particularly in spinal surgery, it is well known to correct an injury, malformation, or other defect using an implanted rod affixed to a body part to be corrected. For example, rod systems have been developed for correcting the positioning of and stabilizing of the spine, and for facilitating fusion at various levels of the spine. In one such system, the rod or elongated implant can be disposed longitudinally along a length of the spine. The rod can be bent, either prior to or during surgery, to correspond to the normal curvature of the spine in the particular region being instrumented, or to such other curvature as the surgeon may deem appropriate to correct the defect. For example, the rod can be bent to form a normal kyphotic curvature for the thoracic region of the spine, or to form a normal lordotic curvature for the lumbar region. The rod can then be attached or engaged to a number of fasteners which have been inserted or implanted into the vertebrae along the segment of the spinal column.

Fasteners are well known in the art and can include all types of bone screws, hooks, bolts, etc. configured to engage the vertebrae. For instance, one such fastener is a laminar hook, configured to engage a lamina of the vertebra. Another prevalent fastener is a spinal screw which can be threaded into a pedicle or other portion of vertebral bone. Examples of spinal screws include monoaxial spinal screws and polyaxial spinal screws.

In some spinal procedures, rods are coupled to two or more fasteners that are fixed to vertebrae, for instance at opposite sides of the spine or spinous processes. The fasteners can be threaded into a portion of several vertebral bodies, such as the pedicles of these vertebrae. The rod can be coupled to the bone screws to provide corrective and stabilizing forces to the spine. Affixing a rod to a fastener generally requires the rod to be in an adjacent position or in contact with the fastener. This may require that the rod and implanted fastener be moved with respect to each other so that the rod occupies space within a channel or other opening in the fastener. The rod can be coupled to the implanted fastener using a set screw, plug or other appropriate closure device. The process of placing a rod within or adjacent to an implanted fastener so that they can be coupled together is termed "reducing" the rod.

SUMMARY

In some embodiments, a lever reducer system is provided. The lever reducer system can include a first tower. The lever reducer system can include a second tower. The lever reducer system can include a lever reducer configured to couple to the first tower and the second tower. In some embodiments, the lever reducer comprises a fulcrum configured to be coupled to the first tower. In some embodiments, the lever reducer comprises a swivel configured to be coupled to the second tower. In some embodiments, the lever reducer is configured to vertically lift the second tower.

In some embodiments, the fulcrum is aligned with the first tower. In some embodiments, the fulcrum is configured to be at least partially inserted into the first tower. In some embodiments, the fulcrum is configured to be at least partially inserted into a lumen of the first tower through which a threaded cap was inserted. In some embodiments, the fulcrum is configured to translate relative to a base of the lever reducer. In some embodiments, the fulcrum is configured to rotate relative to a base of the lever reducer. In some embodiments, the fulcrum comprises a slidable pivot. In some embodiments, the fulcrum is configured to translate in a channel within a base of the lever reducer to accommodate different spans between the first tower and the second tower. In some embodiments, the fulcrum is configured to translate into one or more locking grooves that provide discrete translational positions. In some embodiments, the position of the swivel relative to the fulcrum is configured to allow for mostly vertical motion of the second tower. In some embodiments, the swivel is configured to rotate relative to a base of the lever reducer. In some embodiments, the swivel is configured to rotate in one direction, but rotation in the opposite direction is limited or prevented. In some embodiments, the lever reducer system can include a ratchet mechanism that maintains the vertical lift of the second tower. In some embodiments, a lumen of the second tower is accessible during vertical lift of the second tower.

In some embodiments, a method of using a lever reducer system is provided. The system can include coupling a first tower to a first vertebra. The system can include coupling a second tower to a second vertebra. The system can include coupling a lever reducer to the first tower and the second tower by coupling a fulcrum to the first tower and a swivel to the second tower. The system can include applying a force to the lever reducer to vertically lift the second tower.

In some embodiments, the first vertebra and the second vertebra are lumbar vertebrae. In some embodiments, the method can include translating the fulcrum within a channel of a base of the lever reducer to accommodate different spans between the first tower and the second tower. In some embodiments, the method can include translating the fulcrum within a channel of a base of the lever reducer to accommodate different offsets between the first vertebra and the second vertebra. In some embodiments, the method can include translating the fulcrum into one or more locking grooves that provide discrete translational positions. In some embodiments, the method can include engaging a pawl with a gear to maintain the vertical lift of the second tower. In some embodiments, the method can include securing a rod to a fastener while the lever reducer is coupled to the first tower and the second tower. In some embodiments, the method can include securing a rod to a fastener before coupling the lever reducer to the first tower and the second tower.

BRIEF DESCRIPTION OF THE DRAWINGS

These and other features, aspects and advantages of the described embodiments are described with reference to drawings of certain preferred embodiments, which are intended to illustrate, but not to limit. It is to be understood that the attached drawings are for the purpose of illustrating concepts of the described embodiments and may not be to scale.

FIGS. 15A-15F illustrate movement of the lever reducer system of FIG. 1.

DETAILED DESCRIPTION

Figure 1:
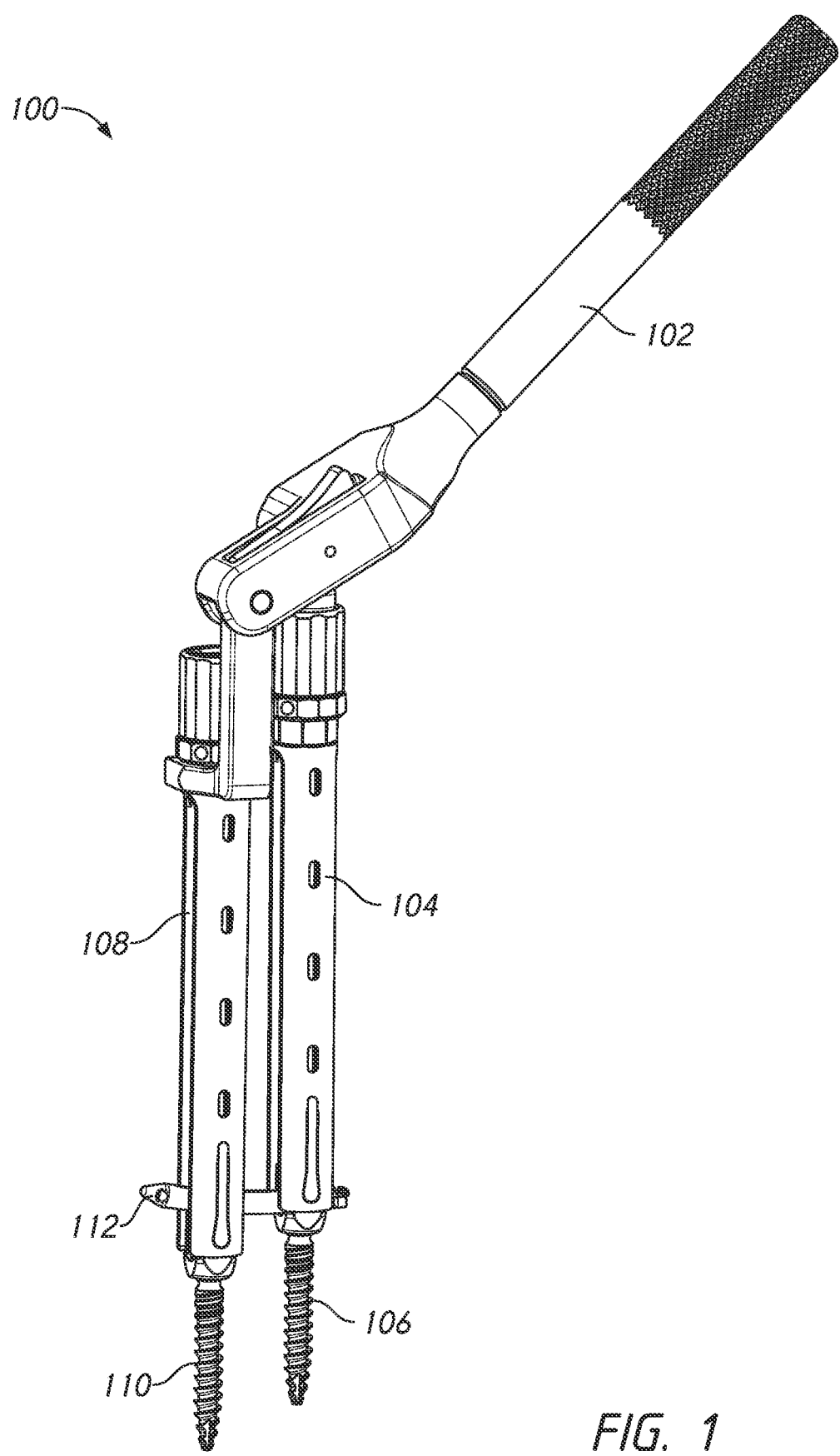
FIG. 1 illustrates a perspective view of a lever reducer system according to an embodiment.

FIG. 1 illustrates a perspective view of an embodiment of a lever reducer system 100. The lever reducer system 100 can include a lever reducer 102. The lever reducer 102 can be utilized to move one component into an adjacent position to another component as described herein. The lever reducer 102 can be reversibly coupled to other components of the lever reducer system 100. The lever reducer 102 can provide leverage to a user to vertically lift a vertebra. The lever reducer 102 can facilitate rod reduction by moving a fastener into alignment with a rod. The lever reducer 102 can have many uses and advantages, as described herein.

The lever reducer system 100 can include a first tower 104. The first tower 104 can be any elongate structure. The first tower 104 can be a component of a tower based screw system. The first tower 104 can be a component of an extended tab screw system. The first tower 104 can be a component of a tower-based screw system or the extended tabs on minimally invasive pedicle screws with breakoff tabs. The first tower 104 can provide access through the skin and tissue of the patient toward a first vertebra. The first tower 104 can be coupled to the lever reducer 102.

The lever reducer system 100 can include a first fastener 106. The first fastener 106 can be coupled to any portion of the spine. The first fastener 106 can be coupled to the first vertebra. The first fastener 106 can have any form or function to engage the vertebra. The first fastener 106 can couple to a pedicle. The first fastener 106 can be a polyaxial screw. The first tower 104 can couple to the first fastener 106. The first tower 104 can couple to a head of the first fastener 106. In some embodiments, the first tower 104 is a separate component from the first fastener 106. The first tower 104 can easily couple and decouple from the first fastener 106. The first tower 104 can include a locking feature to ensure attachment to the first fastener 106. In some embodiments, the first tower 104 is a breakaway tower. In some embodiments, the first tower 104 is integrated with the corresponding first fastener 106. The first tower 104 and the head of the first fastener 106 can be unitarily formed. The first tower 104 and the head of the first fastener 106 can include a score line therebetween. The first tower 104 can easily and cleanly break away at the score line, leaving the head of the first fastener 106 anchored to the first vertebra. The first tower 104 can include extended tabs from the head of the first fastener 106. The extended tabs can be removed in a single motion by applying a force to the extended tabs. The first fastener 106 can be a minimally invasive pedicle screw. The first tower 104 can be breakoff extended tabs. The first tower 104 can provide access to the first fastener 106.

The lever reducer system 100 can include a second tower 108. The first tower 104 and the second tower 108 can be identical. The second tower 108 can be any elongate structure. The second tower 108 can be a component of a tower based screw system. The second tower 108 can be a component of an extended tab screw system. The second tower 108 can be a component of a tower-based screw system or the extended tabs on minimally invasive pedicle screws with breakoff tabs. The second tower 108 can provide access through the skin and tissue of the patient toward a second vertebra. The second tower 108 can be coupled to the lever reducer 102. The second tower 108 can be lifted by the lever reducer 102, as described herein.

The lever reducer system 100 can include a second fastener 110. The first fastener 106 and the second fastener 110 can be identical. The second fastener 110 can be coupled to any portion of the spine. The second fastener 110 can be coupled to the second vertebra. The second fastener 110 can have any form or function to engage the vertebra. The second fastener 110 can couple to a pedicle. The second fastener 110 can be a polyaxial screw. The second tower 108 can couple to the second fastener 110. The second tower 108 can couple to a head of the second fastener 110. In some embodiments, the second tower 108 is a separate component from the second fastener 110. The second tower 108 can easily couple and decouple from the second fastener 110. The second tower 108 can include a locking feature to ensure attachment to the second fastener 110. In some embodiments, the second tower 108 is a breakaway tower. In some embodiments, the second tower 108 is integrated with the corresponding second fastener 110. The second tower 108 and the head of the second fastener 110 can be unitarily formed. The second tower 108 and the head of the second fastener 110 can include a score line therebetween. The second tower 108 can easily and cleanly break away at the score line, leaving the head of the second fastener 110 anchored to the second vertebra. The second tower 108 can include extended tabs from the head of the second fastener 110. The extended tabs can be removed in a single motion by applying a force to the extended tabs. The second fastener 110 can be a minimally invasive pedicle screw. The second tower 108 can be breakoff extended tabs. The second tower 108 can provide access to the second fastener 110.

The lever reducer system 100 can include a rod 112. The rod 112 can be curved. The rod 112 can laterally extend through the first tower 104. The rod 112 can laterally extend through the second tower 108. The rod 112 can slide relative to the towers 104, 108 and toward the vertebrae. The rod 112 can be seated within the head of the first fastener 106. The rod 112 can be secured by a cap to the first fastener 106. The rod 112 can be located within the second tower 108 when the rod 112 is secured to the first fastener 106. The rod 112 can be vertically above the head of the second fastener 110. The rod 112 cannot be secured to the second fastener 110 due to the position of the second fastener 110. The rod 112 cannot be secured to the second fastener 110 due to the position of the second vertebra.

The lever reducer 102 can lift the second tower 108. The lever reducer 102 can lift the second fastener 110. The lever reducer 102 can lift the second vertebra. The lever reducer 102 can raise the second fastener 110 such that the rod 112 can be seated within the head of the second fastener 110.

The lever reducer 102 can raise the second vertebra toward a natural curvature. The lever reducer 102 can raise the second vertebra to correct spondylolisthesis or slippage of the second vertebra. The lever reducer 102 can raise the second vertebra to reduce compression of the spinal nerves. The lever reducer 102 can raise the second vertebra into alignment with the first vertebra.

In some methods, the first vertebra and the second vertebra can be any adjacent vertebrae. In some methods, the first vertebra and the second vertebra are not adjacent vertebrae and have one or more intermediate vertebra therebetween. The first vertebra and the second vertebra can be lumbar vertebrae. In some methods, the first vertebra and the second vertebra can be the L5 and L4 vertebra, respectively. In some methods, the first vertebra and the second vertebra can be the L4 and L5 vertebra, respectively. In some methods, the first vertebra is superior to the second vertebra. In some methods, the first vertebra is inferior to the second vertebra. In some methods, the first vertebra and the second vertebra can be the S1 and L5 vertebra, respectively. In some methods, the first tower 104 is coupled to the sacrum. In some methods, the first fastener 106 is coupled to the sacrum. In some methods, the second tower 108 is coupled to L5. In some methods, the second fastener 110 is coupled to L5. The lumbar vertebra L5 can be lifted relative to the sacrum. In some methods, the first vertebra and the second vertebra can be the L5 and S1 vertebra, respectively. In some methods, the first tower 104 is coupled to L5. In some methods, the first fastener 106 is coupled to L5. In some methods, the second tower 108 is coupled to the sacrum. In some methods, the second fastener 110 is coupled to the sacrum. The sacrum can be lifted relative to the lumbar vertebra L5. The first tower 104 and the first fastener 106 can be coupled to any portion of the spine. The second tower 108 and the second fastener 110 can be coupled to any portion of the spine.

The lever reducer system 100 described herein can be located at any level of the vertebral column. The fasteners 106, 110 can be secured to any vertebrae. The rod 112 can be positioned between any vertebrae. In the description herein, the rod 112 is described as positioned between the first vertebra and the second vertebra. It should be appreciated that the lever reducer system 100 can be utilized in any portion of the spine.

The desired orientation of the rod 112 can depend on the first vertebra and the second vertebra. The rod 112 can restore a natural curvature of the spine. The rod 112 can provide a correction in one or more planes. The rod 112 can fuse the first vertebra and the second vertebra. The rod 112 can be placed at any angle to the transverse plane, including parallel, substantially parallel, perpendicular, substantially perpendicular, 0 degrees, 15 degrees, 30 degrees, 45 degrees, 60 degrees, 75 degrees, 90 degrees, or any range of two of the foregoing values. The rod can be placed at any angle to the sagittal plane, including parallel, substantially parallel, perpendicular, substantially perpendicular, 0 degrees, 15 degrees, 30 degrees, 45 degrees, 60 degrees, 75 degrees, 90 degrees, or any range of two of the foregoing values. The rod can be placed at any angle to the coronal plane, including parallel, substantially parallel, perpendicular, substantially perpendicular, 0 degrees, 15 degrees, 30 degrees, 45 degrees, 60 degrees, 75 degrees, 90 degrees, or any range of two of the foregoing values.

The lever reducer system 100 can facilitate placement of the rod 112 relative to the fasteners 106, 110 by moving one component into an adjacent position to another component. The lever reducer system 100 can facilitate placement of the rod 112 relative to the fasteners 106, 110 by moving the second vertebra with the second fastener 110 into an adjacent position relative to the first vertebra with the first fastener 106. The lever reducer system 100 can facilitate placement of the rod 112 by raising the second fastener 110 to be able to seat the rod 112 within the head of the second fastener 110.

Figure 2:
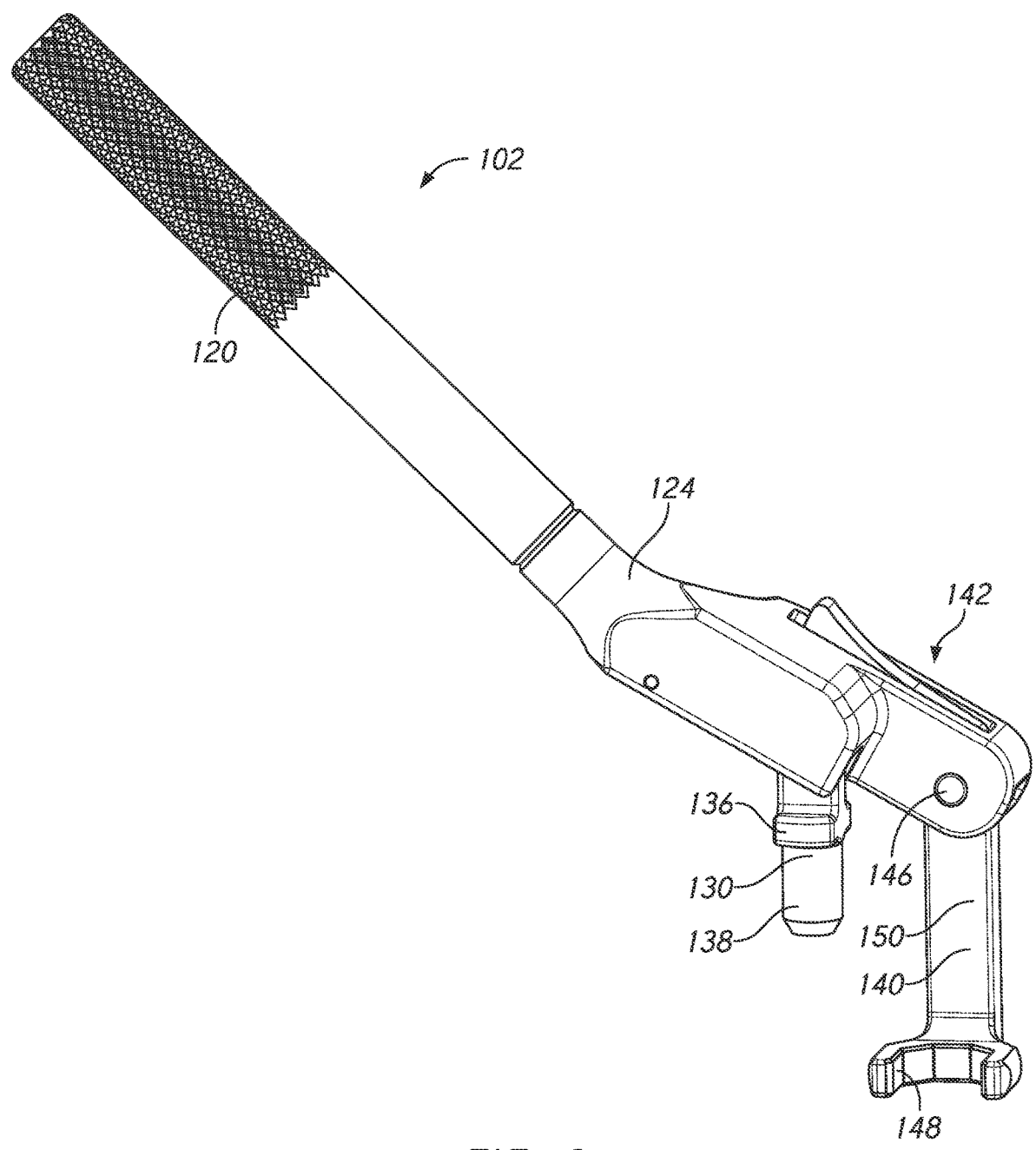
FIG. 2 illustrates a perspective view of a lever reducer of FIG. 1.
Figure 3:
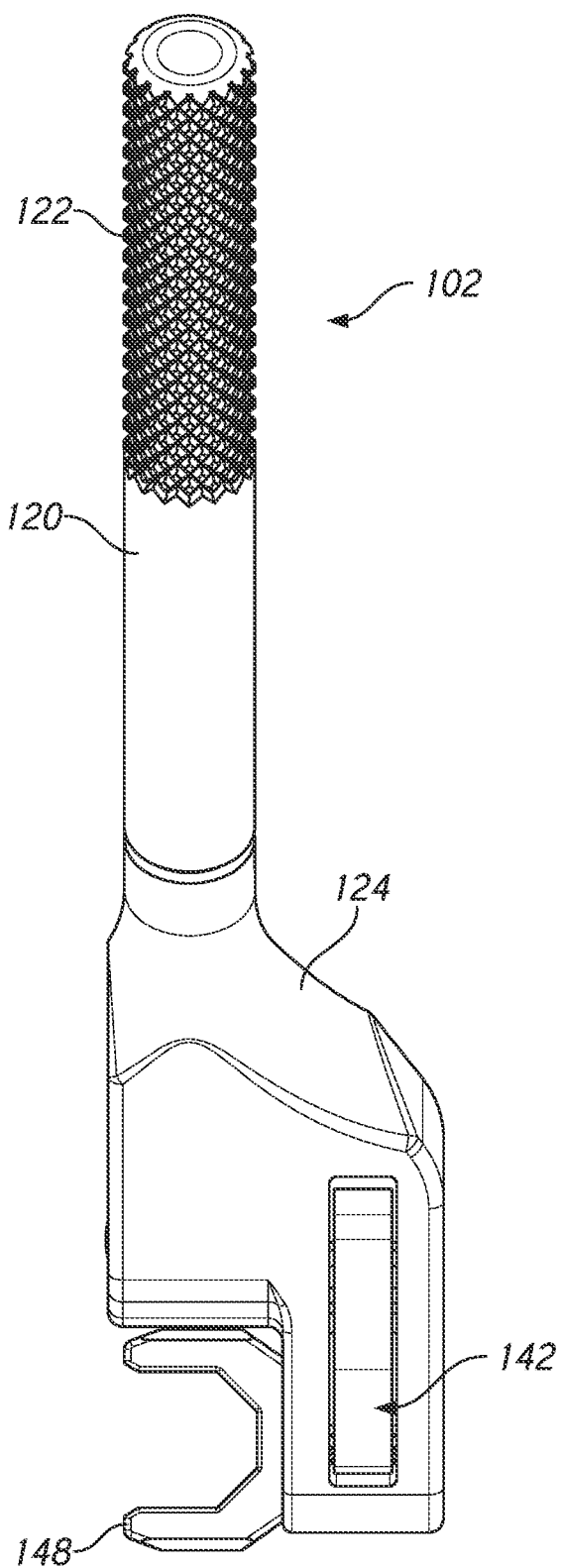
FIG. 3 illustrates a top view of the lever reducer of FIG. 1.
Figure 4:
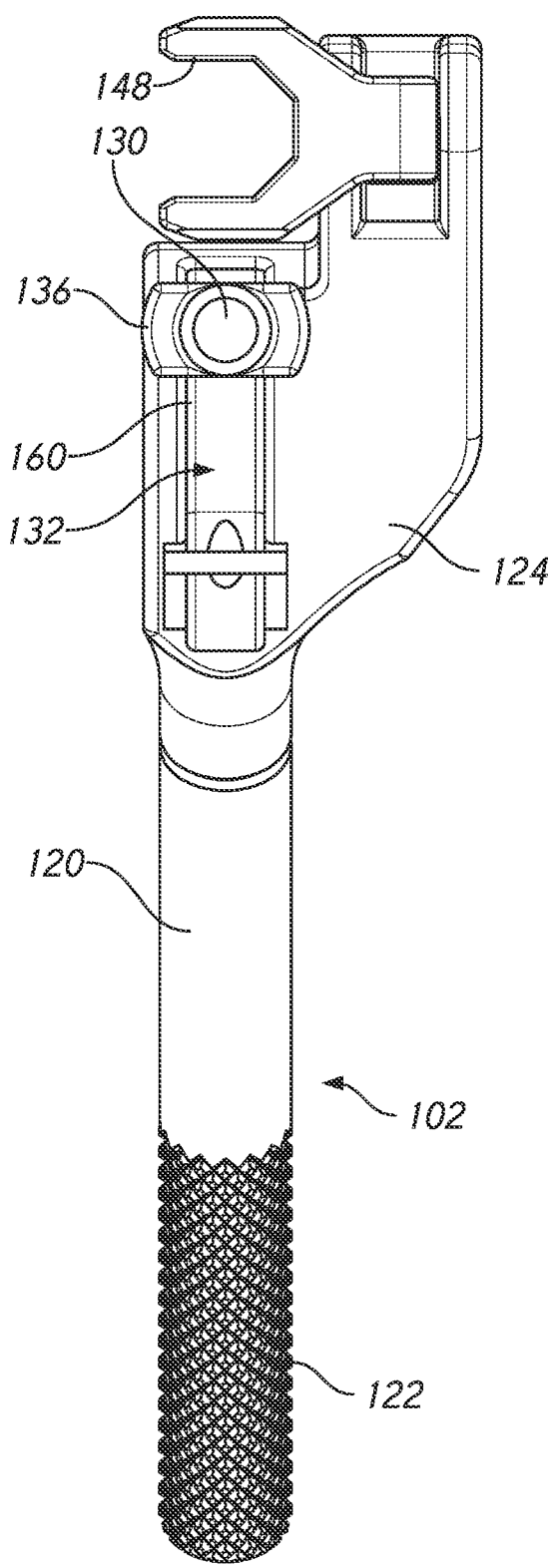
FIG. 4 illustrates a bottom view of the lever reducer of FIG. 1.
Figure 5:
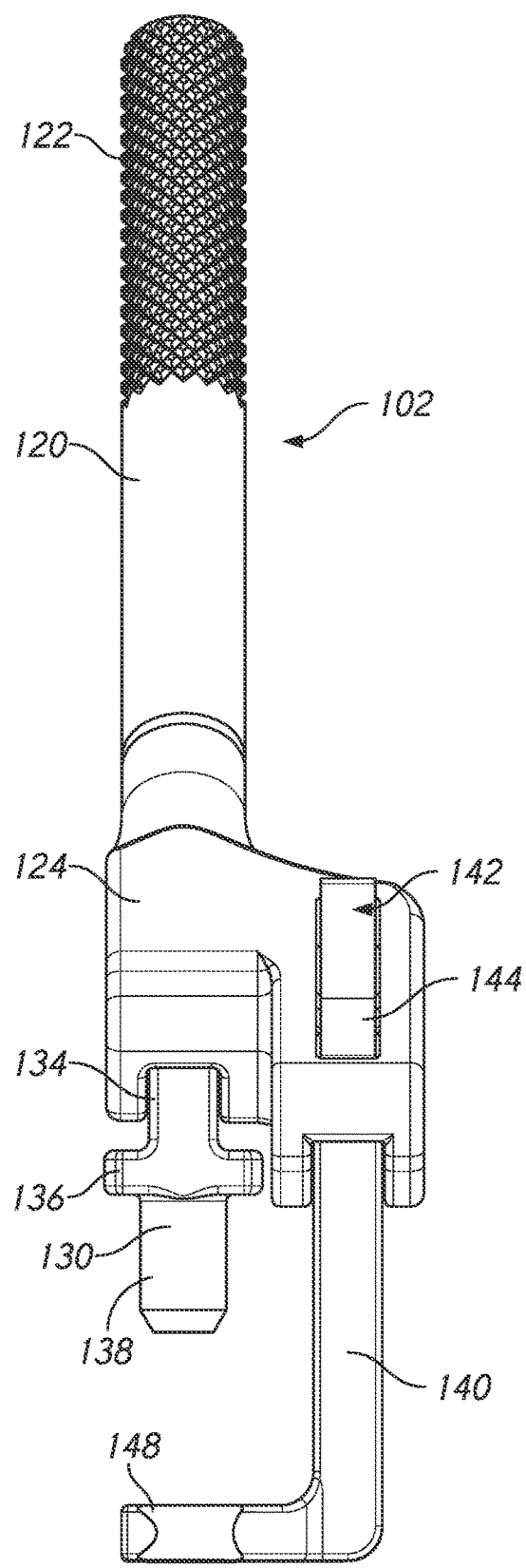
FIG. 5 illustrates a front view of the lever reducer of FIG. 1.

FIG. 2 illustrates a perspective view of the lever reducer 102. FIG. 3 illustrates a top view of the lever reducer 102. FIG. 4 illustrates a bottom view of the lever reducer 102. FIG. 5 illustrates a front view of the lever reducer 102.

The lever reducer 102 can include a handle 120. The handle 120 can include a grip 122. The grip 122 can be a knurled surface. The grip 122 can be a textured surface. The grip 122 can have any feature to facilitate manipulation by a user. The handle 120 can be removable. In some embodiments, the handle 120 can include a threaded tip. The handle 120 can couple to a base 124. The base 124 can include a threaded bore to engage the threaded tip of the handle 120. In some embodiments, the base 124 includes a threaded tip and the handle 120 includes a threaded bore. In some embodiments, the handle 120 and the base 124 are integrally or monolithically formed. The handle 120 can be angled relative to the base 124. The handle 120 can form an angle relative to the base 124 of 0 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 0 degrees and 20 degrees, between 10 degrees and 30 degrees, less than 45 degrees, less than 60 degrees, or any range of two of the foregoing values.

The lever reducer 102 can include a fulcrum 130. The lever reducer 102 can include a first engagement feature 132. The base 124 can include the first engagement feature 132. The first engagement feature 132 can include a main translational channel 160. The first engagement feature 132 can allow the fulcrum 130 to translate relative to the base 124. The first engagement feature 132 can allow the fulcrum 130 to translate linearly. The first engagement feature 132 can allow the fulcrum 130 to translate a distance relative to the base 124. In some embodiments, the fulcrum 130 can translate relative to the base 124 a distance of 0 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, between 5 mm and 15 mm, between 10 mm and 20 mm, between 15 mm and 30 mm, up to 10 mm, up to 15 mm, or any range of two of the foregoing values.

The first engagement feature 132 can allow the fulcrum 130 to rotate relative to the base 124. The first engagement feature 132 can allow the fulcrum 130 to rotate and translate simultaneously. The first engagement feature 132 can allow the fulcrum 130 to rotate without translation. In some embodiments, the fulcrum 130 can rotate relative to the base 124 to form an angle of 0 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, between 45 degrees and 90 degrees, between 30 degrees and 120 degrees, greater than 45 degrees, greater than 60 degrees, or any range of two of the foregoing values.

In some embodiments, the fulcrum 130 can rotate relative to the base 124 a greater degree in a distal position of the fulcrum 130. The base 124 can include a recess 134. The recess 134 can allow the fulcrum 130 to rotate relative to the base 124 to form an angle of 90 degrees, 95 degrees, 100 degrees, 105 degrees, 110 degrees, 115 degrees, 120 degrees, 130 degrees, 135 degrees, 140 degrees, 145 degrees, 150 degrees, 155 degrees, 160 degrees, 165 degrees, 170 degrees, 175 degrees, 180 degrees, 185 degrees, 190 degrees, 195 degrees, 200 degrees, 205 degrees, 210 degrees, 215 degrees, 220 degrees, 230 degrees, 235 degrees, 240 degrees, 245 degrees, 250 degrees, 255 degrees, 260 degrees, 265 degrees, 270 degrees, between 180 degrees and 270 degrees, between 90 degrees and 180 degrees, greater than 90 degrees, greater than 120 degrees, or any range of two of the foregoing values.

The fulcrum 130 can include a bearing surface 136. The bearing surface 136 can rest against the first tower 104. The bearing surface 136 can include one or more ridges. The bearing surface 136 can be continuous around the fulcrum 130. The bearing surface 136 can be a ring. The bearing surface 136 can be discontinuous around the fulcrum 130. The bearing surface 136 can be a pair of tabs. The bearing surface 136 can be two diametrically opposed tabs.

The fulcrum 130 can include an insertion surface 138. The insertion surface 138 can be below the bearing surface 136. The insertion surface 138 can be inserted into the first tower 104. The distal end of the fulcrum 130 can be tapered to facilitate insertion into the first tower 104. The insertion surface 138 can have a tapered end. The insertion surface 138 can be cylindrical. The insertion surface 138 can be the same or similar cross-section as a cross-section of a lumen of the first tower 104. The insertion surface 138 can have circular or rounded cross-section. In some embodiments, the fulcrum 130 can rotate within the first tower 104. The fulcrum 130 can have an infinite number of rotational orientations relative to the first tower 104. In some embodiments, the insertion surface 138 can have non-circular cross-section. The insertion surface 138 can have a keyed cross-section. In some embodiments, the fulcrum 130 cannot rotate within the first tower 104. The fulcrum 130 can have a discrete number of rotational orientations relative to the first tower 104. The fulcrum 130 can have one rotational orientation relative to the first tower 104.

The lever reducer 102 can include a swivel 140. The lever reducer 102 can include a second engagement feature 142. The second engagement feature 142 can be ratchet mechanism. The second engagement feature 142 can include an actuator 144. The second engagement feature 142 can include a pin 146. The actuator 144 and the pin 146 can couple to the base 124. The second engagement feature 142 can allow the swivel 140 to rotate relative to the base 124. The second engagement feature 142 can prevent the swivel 140 from translating. The second engagement feature 142 can maintain the rotational position of the swivel 140. The second engagement feature 142 can allow rotational motion of the swivel 140 in a first direction. The second engagement feature 142 can prevent rotational motion of the swivel 140 in a second direction, opposite the first direction. In some embodiments, the second engagement feature 142 can allow clockwise rotation of the swivel 140 but prevent counter-clockwise rotation of the swivel 140. The second engagement feature 142 can maintain a rotational position of the swivel 140.

The second engagement feature 142 can allow the swivel 140 to rotate without translation. In some embodiments, the swivel 140 can rotate relative to the base 124 to form an angle of 0 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, between 45 degrees and 90 degrees, between 30 degrees and 120 degrees, greater than 45 degrees, greater than 60 degrees, or any range of two of the foregoing values. The second engagement feature 142 can allow the swivel 140 to travel in an arc.

The swivel 140 can include a gripping surface 148. The gripping surface 148 can be inserted around the second tower 108. The second tower 108 can include a keyed surface. The second tower 108 can have a polygonal surface including two flats, three flats, four flats, five flats, six flats, seven flats, eight flats, nine flats, ten flats, eleven flats, twelve flats, between six flats and eight flats, or any range of two of the foregoing values. The gripping surface 148 can have a keyed socket. The gripping surface 148 can have a polygonal surface including two flats, three flats, four flats, five flats, six flats, seven flats, eight flats, between two flats and four flats, or any range of two of the foregoing values. The gripping surface 148 can have the form of an open-end wrench.

The gripping surface 148 can be the same or similar cross-section as a cross-section of the second tower 108. The gripping surface 148 can have non-circular cross-section. The gripping surface 148 can have a keyed cross-section. In some embodiments, the gripping surface 148 cannot rotate relative to the second tower 108. The gripping surface 148 can have a discrete number of rotational orientations relative to the second tower 108. The gripping surface 148 can have one rotational orientation relative to the second tower 108. In some embodiments, the gripping surface 148 can have circular or rounded cross-section. The gripping surface 148 can rotate relative to the second tower 108. The gripping surface 148 can have an infinite number of rotational orientations relative to the second tower 108.

The swivel 140 can have an L-shape geometry. The swivel 140 can have an extension 150. The extension 150 can align with the actuator 144. The gripping surface 148 can be laterally offset. The gripping surface 148 can be offset from the actuator 144. The gripping surface 148 can be perpendicular to the extension 150.

The lever reducer 102 can have features aligned generally along a longitudinal axis of the lever reducer 102 that facilitate the application of a force. In some embodiments, the handle 120 can be aligned with the first engagement feature 132. In some embodiments, the handle 120 can be aligned with the fulcrum 130. This alignment can prevent a torque on the fulcrum 130 when a force is applied to the handle 120. In some embodiments, the handle 120 can be aligned with the first tower 104. This alignment can prevent a torque on the first tower 104 when a force is applied to the handle 120. In some embodiments, the handle 120 can be aligned with the second tower 108. This alignment can prevent a torque on the second tower 108 when a force is applied to the handle 120. The first tower 104 and the second tower 108 can be aligned with each other. The shape of the swivel 140 can position the second tower 108 to be aligned with the first tower 104.

The first tower 104 and the second tower 108 can be aligned with the fulcrum 130. The fulcrum 130 is the support about which the lever reducer 102 pivots, as described herein. The handle 120 can be aligned with the fulcrum 130. The handle 120 and the base 124 act as a lever to pivot about the fulcrum 130. The handle 120 and the base 124 are a rigid body which pivots. As the handle 120 and a portion of the base 124 proximal to the fulcrum 130 are lowered, the portion of the base 124 distal to the fulcrum 130 raises.

The lever reducer 102 can include the first engagement feature 132 and the second engagement feature 142 which facilitate this pivoting. The first engagement feature 132 can allow rotation and translation of the fulcrum 130. In some embodiments, the fulcrum 130 is a movable pivot. The second engagement feature 142 can allow rotation of the swivel 140. In some embodiments, the swivel 140 allows rotation in a first direction but prevents or limits rotation in a second direction, opposite the first direction. Additional features of the first engagement feature 132 and the second engagement feature 142 are described herein.

Figure 6:
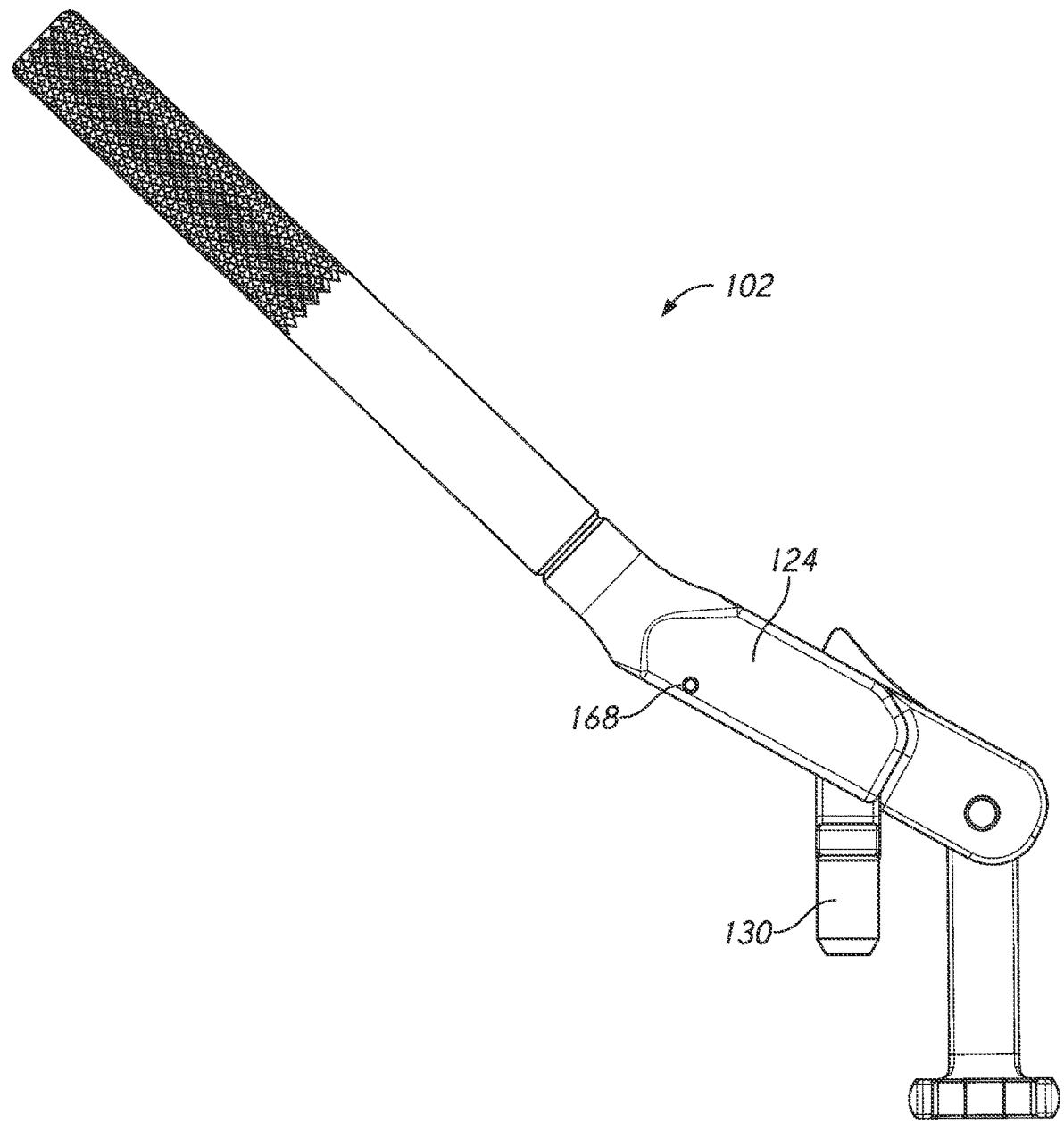
FIG. 6 illustrates a first side view of the lever reducer of FIG. 1.
Figure 7:
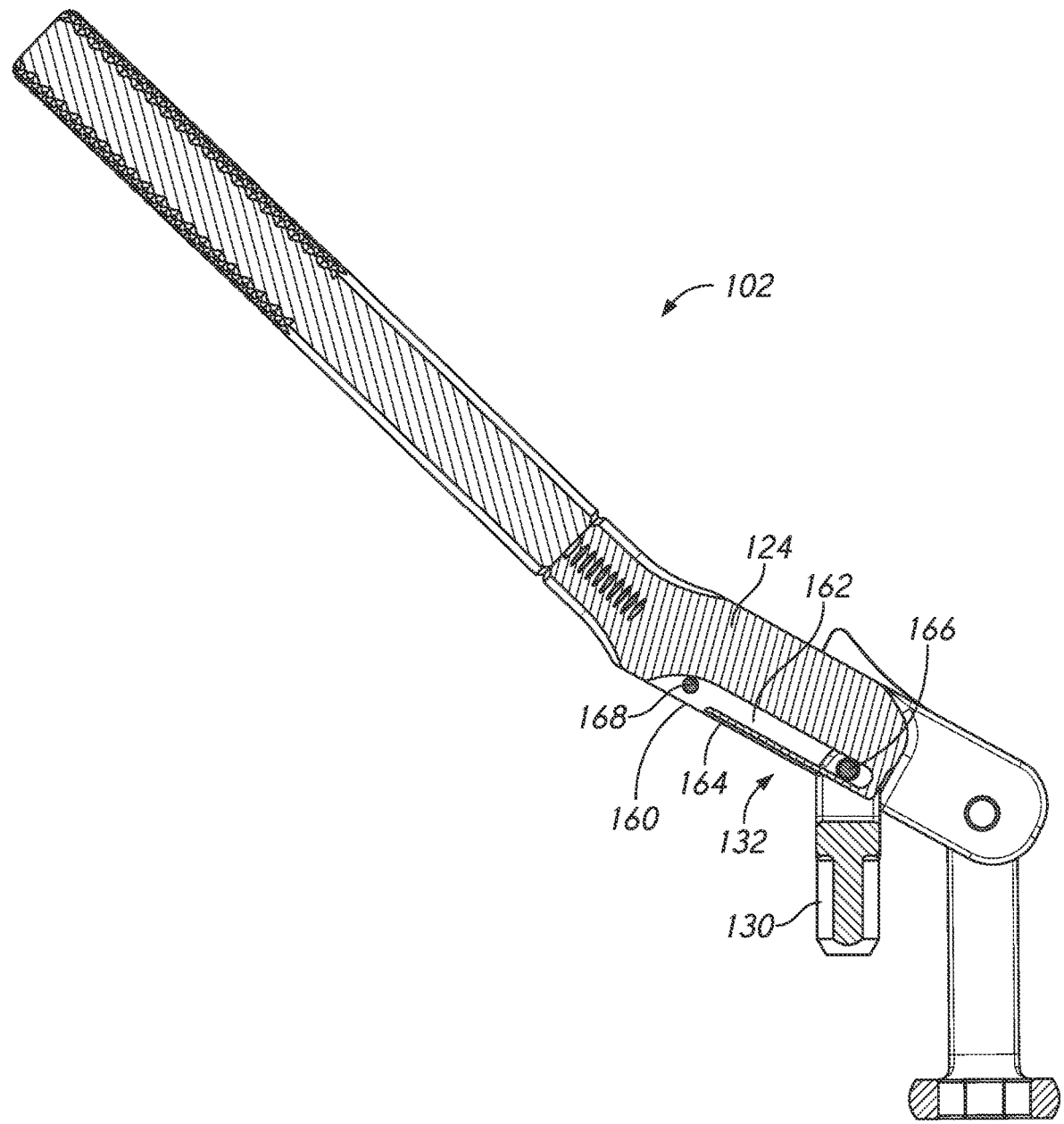
FIG. 7 illustrates a cross-sectional view of the lever reducer of FIG. 1.
Figure 8:
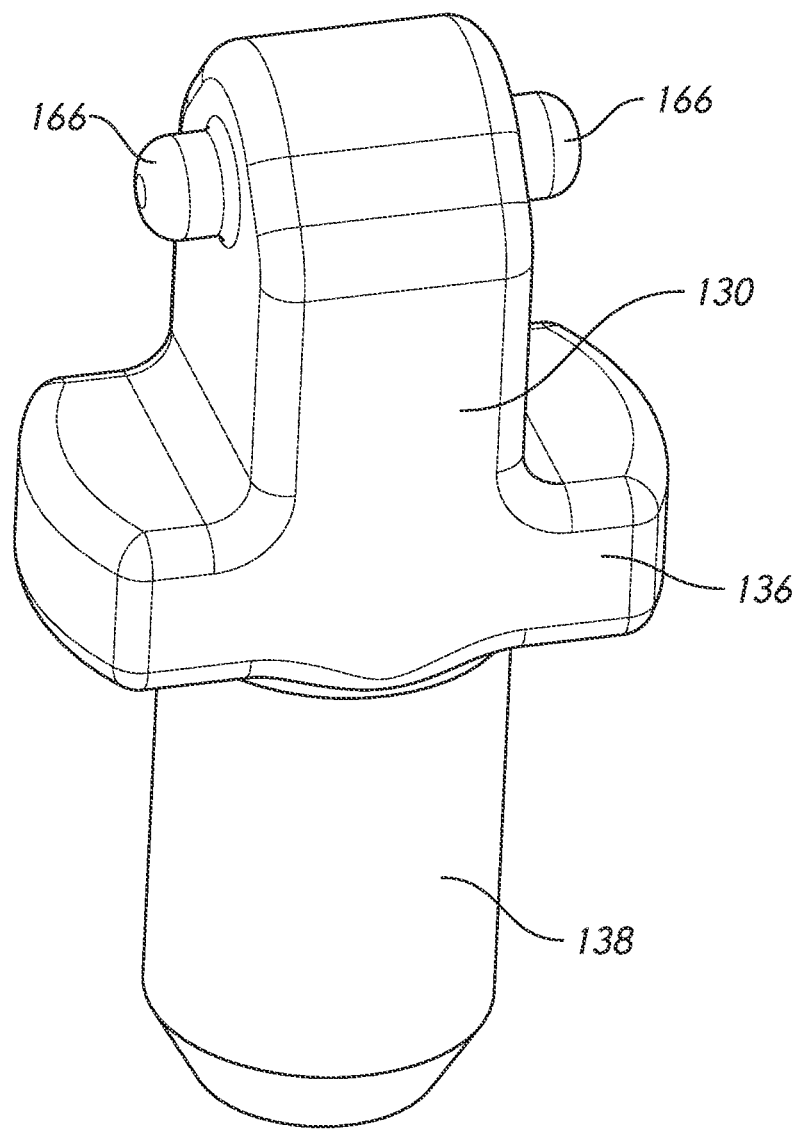
FIG. 8 illustrates a fulcrum of the lever reducer of FIG. 1.

FIG. 6 illustrates a first side view of the lever reducer 102. FIG. 7 illustrates a cross-sectional view of the lever reducer 102. FIG. 8 illustrates the fulcrum 130 of the lever reducer 102.

The first engagement feature 132 can include the main translational channel 160. The main translational channel 160 can be linear. The main translational channel 160 can be non-linear. The main translational channel 160 can form an arc. The first engagement feature 132 can include a pair of side channels 162. The side channels 162 can extend along sides of the main translational channel 160. The side channels 162 can extend the entire length of the main translational channel 160. The side channels 162 can extend along a portion of the length of the main translational channel 160. The first engagement feature 132 can include a pair of flanges 164. The pair of flanges 164 can extend along sides of the main translational channel 160. The pair of flanges 164 can extend under the side channels 162. The pair of flanges 164 can extend the entire length of the main translational channel 160. The pair of flanges 164 can extend along a portion of the length of the main translational channel 160.

The fulcrum 130 can include a pair of pivots 166. The pair of pivots 166 can be axially aligned. The pair of pivots 166 can be diametrically opposed. The pair of pivots 166 can form a pivot pin. The fulcrum 130 and the pair of pivots 166 can be integrally or monolithically formed. In some embodiments, the fulcrum 130 can include a bore configured to receive a pivot pin. The fulcrum 130 and the pair of pivots 166 or other pivot pin can be separately formed. The pair of pivots 166 can be cylindrical. The pair of pivots 166 can include rounded edges. The pair of pivots 166 can be semi-spherical.

The pair of pivots 166 extend into the pair of side channels 162 of the base 124. Each pivot 166 slides along the side channels 162 as the fulcrum 130 slides. Each pivot 166 is retained within the side channel 162 by the flange 164 as the fulcrum 130 slides. Each pivot 166 slides along the flange 164. The bearing surface 136 and the insertion surface 138 extend from the main translational channel 160 as the fulcrum 130 slides. The fulcrum 130 freely translates proximally and distally as the pair of pivots 166 is retained in the side channels 162.

The pair of pivots 166 can rotate within the pair of side channels 162. Each pivot 166 is retained within the side channel 162 by the flange 164 as the fulcrum 130 rotates. Each pivot 166 rotates relative to the flange 164. The shape of the pair of pivots 166 can facilitate rotation. The fulcrum 130 can rotate relative to the base 124. The fulcrum 130 can translate relative to the base 124. The fulcrum 130 can rotate and translate relative to the base 124.

In some embodiments, the pair of pivots 166 can translate within the first engagement feature 132 in discrete steps. The first engagement feature 132 can include one or more locking grooves that provide discrete translational positions. The first engagement feature 132 can include two locking grooves, three locking grooves, four locking grooves, five locking grooves, six locking grooves, seven locking grooves, eight locking grooves, nine locking grooves, ten locking grooves, or any range of two of the foregoing values. The first engagement feature 132 can include any number of locking grooves. The locking grooves can be formed in the pair of flanges 164. The locking grooves can be formed in the pair of side channels 162. The locking grooves can be formed in the main translational channel 160. The locking grooves can be separately formed from the components of the first engagement feature 132. The locking grooves can interact with the pair of pivots 166 of the fulcrum 130. The pair of pivots 166 can slide distally and proximally to engage the next locking groove. The locking groove can apply a frictional force to retain the pair of pivots 166. The pair of pivots 166 can overcome the frictional force by a force applied by the user. The pair of pivots 166 can overcome the frictional force by movement of one component relative to another.

The fulcrum 130 can include the bearing surface 136 configured to rest against the first tower 104. The bearing surface 136 can include a pair of tabs. The pair of pivots 166 can be above the bearing surface 136. The pair of pivots 166 can be aligned with the pair of tabs of the bearing surface 136. The pair of pivots 166 and the bearing surface 136 can prevent or limit a left-right rocking motion of the fulcrum 130. The insertion surface 138 can prevent or limit a left-right rocking motion of the fulcrum 130. The pair of pivots 166 and the pair of side channels 162 can limit the motion of the fulcrum 130 to proximal-distal translation within the main translational channel 160. The pair of pivots 166 and the side channels 162 can limit the motion of the fulcrum 130 to rotation within the main translational channel 160. The rotation can be swinging in the proximal-distal direction. The shape of the fulcrum 130 can limit or reduce any other motion between the base 124 and the fulcrum 130.

The lever reducer 102 can include a retention pin 168. The retention pin 168 can prevent disengagement between the fulcrum 130 and the base 124. The retention pin 168 can function as a proximal stop for the translation of the fulcrum 130. The retention pin 168 can be inserted after the pair of pivots 166 are inserted within the pair of side channels 162.

Figure 9:
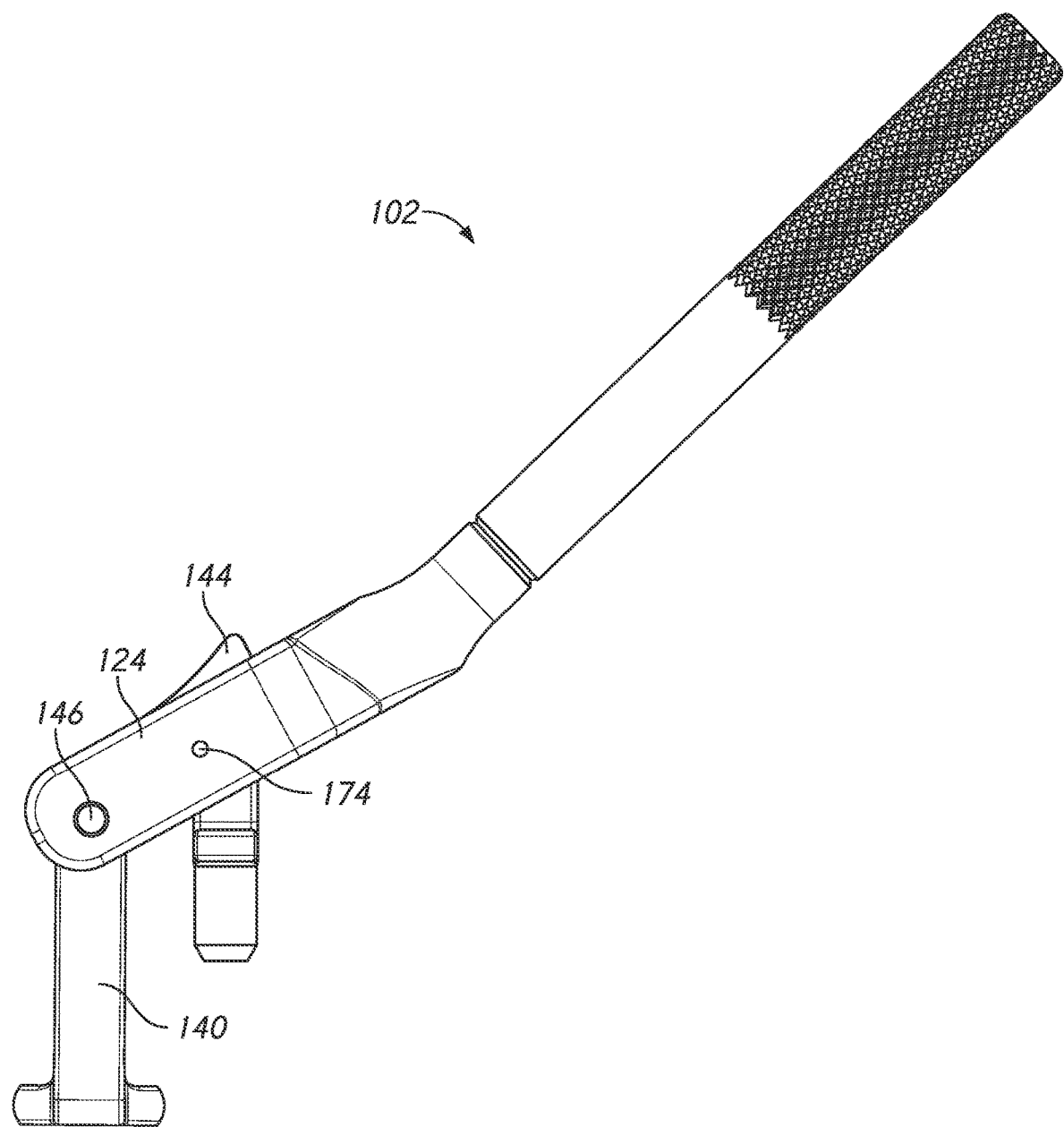
FIG. 9 illustrates a second side view of the lever reducer of FIG. 1.
Figure 10:
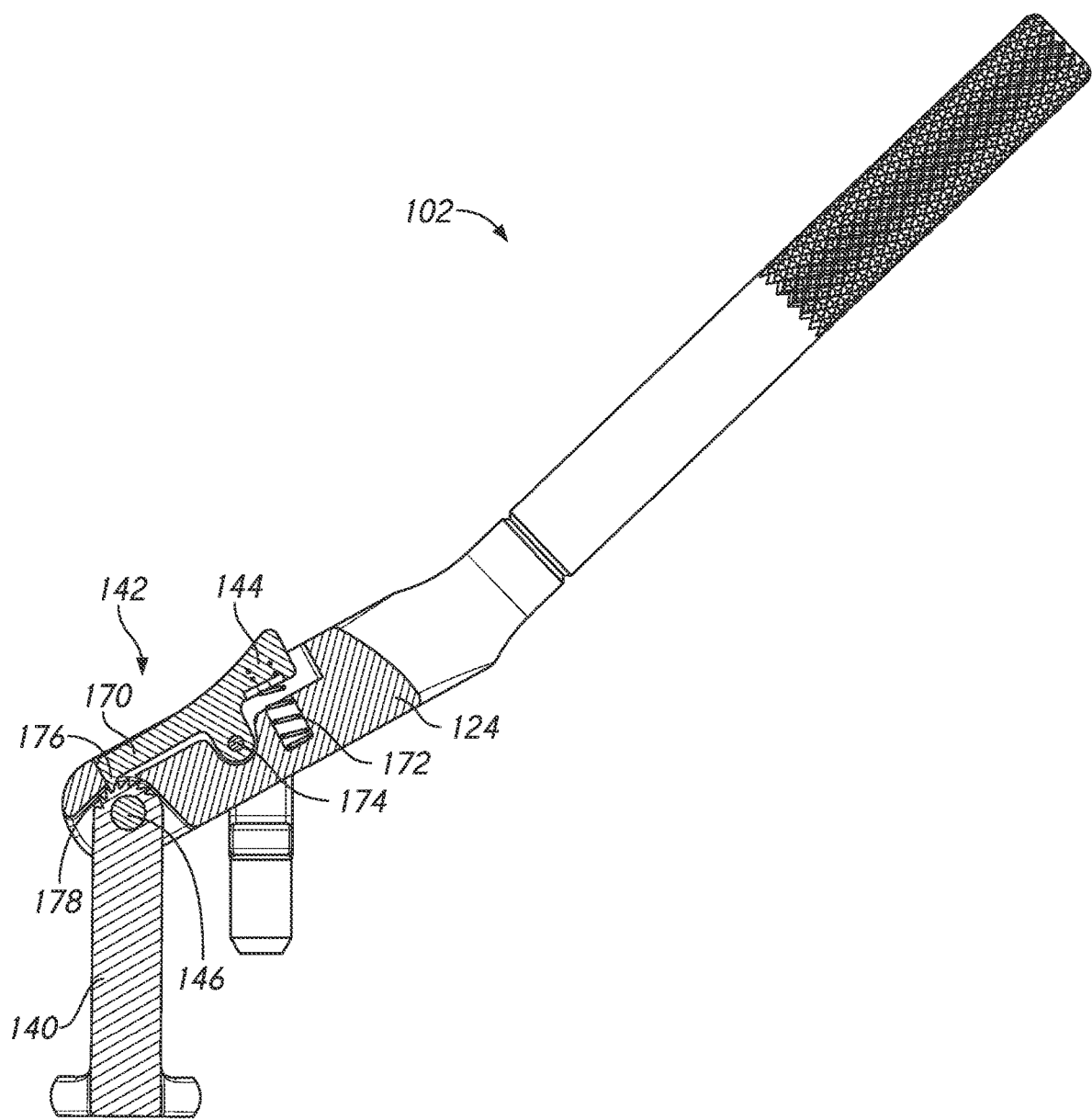
FIG. 10 illustrates a cross-sectional view of the lever reducer of FIG. 1.
Figure 11:
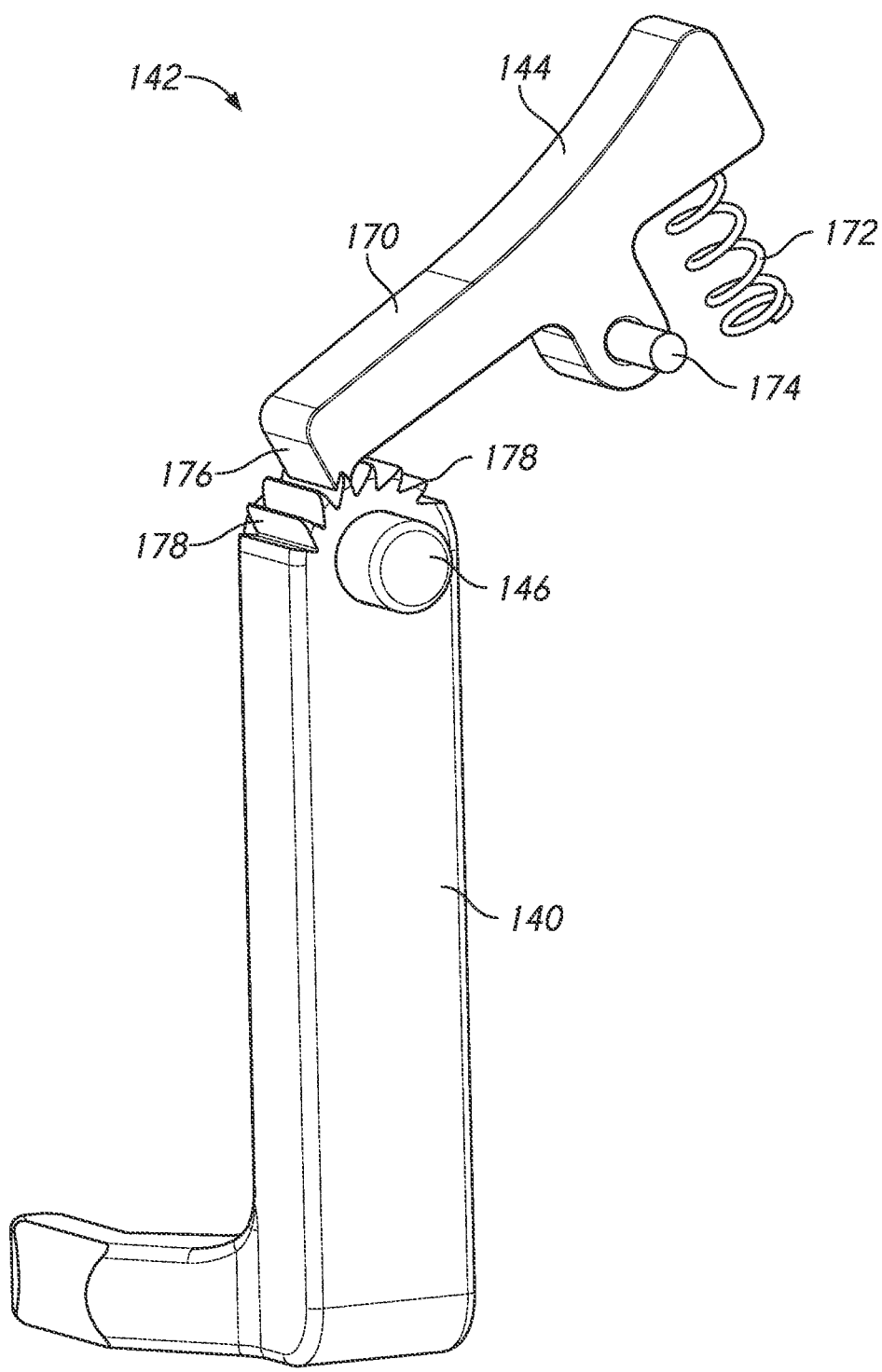
FIG. 11 illustrates an actuator of the lever reducer of FIG. 1.

FIG. 9 illustrates a second side view of the lever reducer 102. FIG. 10 illustrates a cross-sectional view of the lever reducer 102. FIG. 11 illustrates the actuator 144 of the lever reducer 102.

The second engagement feature 142 can include the actuator 144. The actuator 144 can be actuated by the user. The actuator 144 can be automatically actuated. The actuator 144 can include a lever arm 170. The lever arm 170 can be biased. The actuator 144 can include a spring 172. The actuator 144 can include a pivot pin 174. The lever arm 170 can pivot relative to the pivot pin 174. The pivot pin 174 can couple the lever arm 170 to the base 124. As the lever arm 170 is pivoted, the spring 172 can be compressed. The lever arm 170 can include a pawl 176. The pawl 176 can function as a ratchet.

The swivel 140 can include one or more gears 178. The gears 178 can be radial gears. The gears 178 can be ramped. The gears 178 can form a wedge. The gears 178 can be asymmetric. The gears 178 can allow movement in one direction but prevent movement in another direction. The gears 178 can allow the pawl 176 to slide along the ramped surface of the gears 178 and into the next gear. The gears 178 can prevent the pawl 176 from moving in the opposite direction. The ramped surface of the gears 178 forms a wall or wedge to prevent movement of the pawl 176 in the opposite direction.

The second engagement feature 142 can include the pin 146. The pin 146 can couple the swivel 140 to the base 124. The swivel 140 can rotate relative to the base 124. The swivel 140 can rotate in a first direction. The pawl 176 slides along a gear 178 thereby depressing the spring 172. The pawl 176 slides along a gear 178 until falling to the next gear 178. The spring 172 biases the lever arm 170 down into engagement with the groove of the gear 178. The pawl 176 slides along the next gear 178 thereby depressing the spring 172. The pawl 176 slides along a gear 178 until falling to the next gear 178. The pawl 176 freely advances in a first direction. The pawl 176 can be limited or prevented from advancing in the opposite direction. The shape of the gears 178 provide a wedge preventing rotational movement in the opposite direction. The pawl 176 cannot vertically clear the wedge of the gear 178. The spring 172 biases the pawl 176 downward preventing rotational movement in the opposite direction.

The second engagement feature 142 can allow the swivel 140 to rotate relative to the base 124 in one direction. The second engagement feature 142 provides a ratchet that limits rotational movement. The shape of the pawl 176 and the gears 178 allows rotation in one direction, but limits rotation in the opposite direction. The biasing force of the spring 172 allows rotation in one direction, but limits rotation in the opposite direction. The swivel 140 rotates about the pin 146 relative to the base 124. The swivel 140 can form a slight arc during vertical motion as described herein. The second engagement feature 142 can prevent the swivel 140 from translating relative to the base 124.

The second engagement feature 142 can maintain the rotational position of the swivel 140. The second engagement feature 142 can maintain the correction between the first tower 104 and the second tower 108. The second engagement feature 142 can maintain the correction between the vertebrae as the second vertebra is lifted. The shape of the pawl 176 and the gears 178 can maintain the rotation position during vertical lift. The biasing force of the spring 172 can maintain the rotation position during vertical lift.

Figure 12:
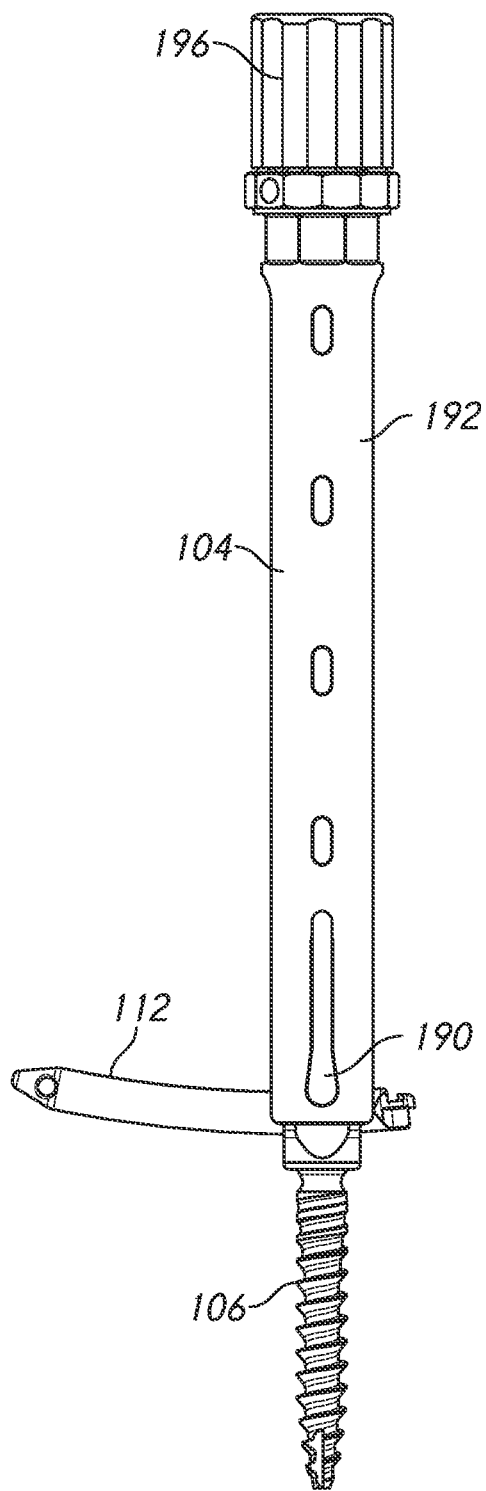
FIG. 12 illustrates a first tower of the lever reducer system of FIG. 1.
Figure 13:
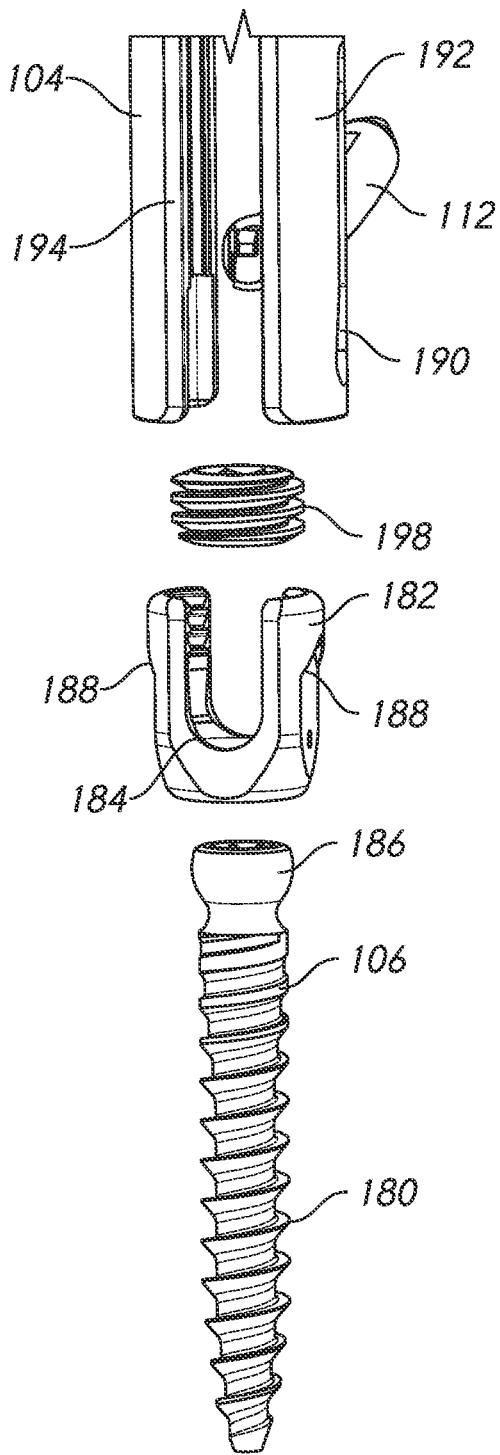
FIG. 13 illustrates exploded components of the lever reducer system of FIG. 1.
Figure 14:
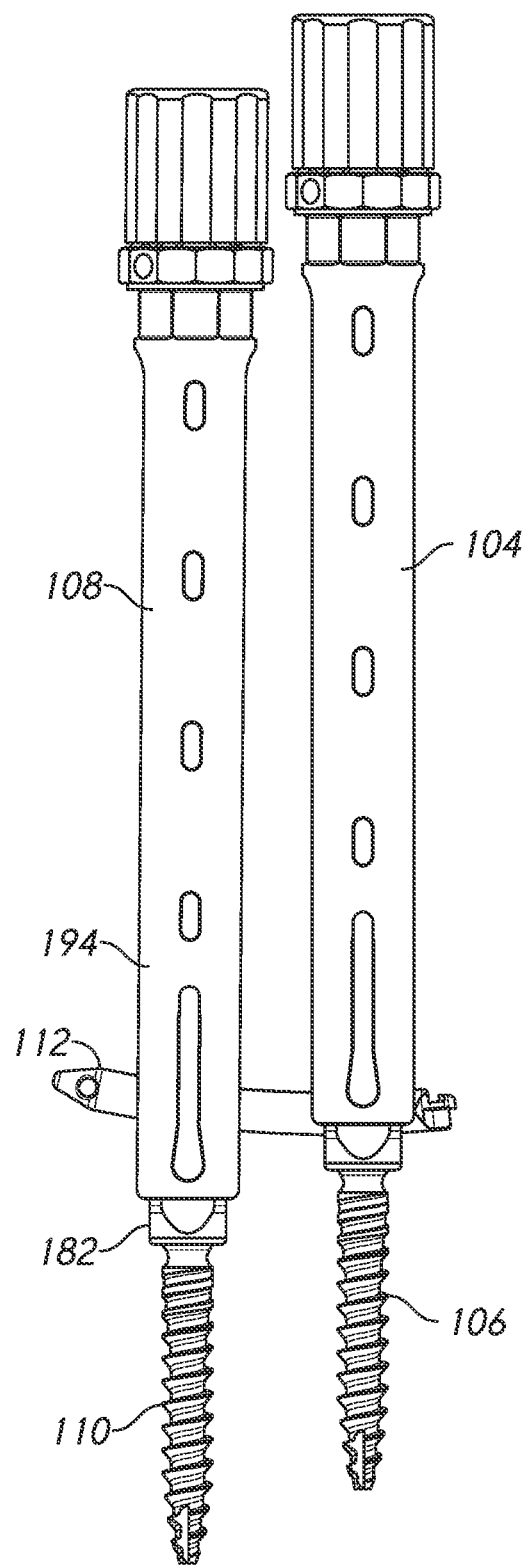
FIG. 14 illustrates the first tower and a second tower of the lever reducer system of FIG. 1.

FIG. 12 illustrates the first tower 104 of the lever reducer system 100. FIG. 13 illustrates exploded components of the lever reducer system 100. FIG. 14 illustrates the first tower 104 and the second tower 108 of the lever reducer system 100. The first tower 104 and the second tower 108 facilitate placement of the rod 112. The rod 112 can be generally straight. The rod 112 can include a bend. The bend can correspond to a bend of the vertebrae. The bend can correspond to a desired curvature of the spine. The bend can correspond to a desired spinal correction. The bend can correspond to a desired lift of the second vertebra.

In some methods, the first fastener 106 is coupled to the first vertebra. The first vertebra can be any vertebra along the spine of the patient. The first fastener 106 can include a threaded shaft 180. The first fastener 106 can be rotated to engage the first vertebra. The first fastener 106 can be positioned to engage cortical bone. In some methods, the first fastener 106 engages the pedicle. The pedicle is a portion of the vertebra between the transverse process and the vertebral body. The pedicle can be used as an anchoring point for fasteners in spinal procedures. In other methods, the first fastener 106 engages another portion of the first vertebra. The first fastener 106 can couple to the spinal process. The first fastener 106 can couple to the transverse process. The first fastener 106 can couple to the lamina. The first fastener 106 can be coupled to any portion of the first vertebra.

The first fastener 106 can include a head 182. The head 182 can include a slot 184 sized and configured to receive the rod 112. The head 182 can have polyaxial movement relative to the threaded shaft 180. The threaded shaft 180 can have a bulbous surface 186. The head 182 can receive the bulbous surface 186 of the threaded shaft 180. The head 182 can move within a range of motion relative to the threaded shaft 180. The head 182 can rotate relative to the threaded shaft 180. The head 182 can tilt relative to the threaded shaft 180. The polyaxial movement between the threaded shaft 180 and the head 182 can facilitate a range of orientations for the first fastener 106. The polyaxial movement between the threaded shaft 180 and the head 182 can facilitate a range of orientations for the rod 112. In some embodiments, the head 182 can have no movement relative to the threaded shaft 180. In some embodiments, the head 182 can have only monoaxial movement relative to the threaded shaft 180.

The first tower 104 can couple to the first fastener 106. The first tower 104 can couple to the first fastener 106 after the first fastener 106 is coupled to the first vertebra. In other methods, the first tower 104 can couple to the first fastener 106 before the first fastener 106 is coupled to the first vertebra. The first tower 104 can couple to the head 182. The head 182 can include a pair of recesses 188. The first tower 104 can include a pair of arms 190. The pair of arms 190 can engage the pair of recesses 188 to couple the first tower 104 to the first fastener 106. The pair of arms 190 can be deflected radially outward to accommodate the head 182 therebetween. The pair of arms 190 can be biased inward into engagement with the pair of recesses 188.

In some embodiments, the first tower 104 and the head 182 are integrally or monolithically formed. In some embodiments, the first tower 104 and the first fastener 106 are integrally or monolithically formed. The threaded shaft 180 can have no movement relative to the combined head 182 and the tower 104. The threaded shaft 180 can have monoaxial movement relative to the combined head 182 and the tower 104. The threaded shaft 180 can have polyaxial movement relative to the combined head 182 and the tower 104. The first tower 104 can decouple from the first fastener 106 after the rod 112 is secured. The first tower 104 can include a score line indicating that location of the decoupling.

The first tower 104 can include a shaft 192. The shaft 192 can include a slot 194 sized to receive the rod 112. In some methods, the rod 112 can slide toward the first fastener 106. In some methods, the rod 112 is inserted into the head 182 without sliding vertically in the slot 194. In some methods, the rod 112 is inserted along a trajectory.

The first tower 104 can include a tower cap 196. The tower cap 196 can rotate relative to the shaft 192. The tower cap 196 can translate relative to the shaft 192. The tower cap 196 can rotate and translate to control the engagement of the pair of arms 190 with the pair of recesses 188. The tower cap 196 can rotate and translate to control the coupling of the first tower 104 and the first fastener 106. The tower cap 196 can rotate and translate to disengage the pair of arms 190 with the pair of recesses 188. The tower cap 196 can rotate and translate to control the decoupling of the first tower 104 and the first fastener 106.

In some methods, the rod 112 is seated within the first fastener 106. The shaft 192 and the tower cap 196 can form a lumen therethrough. The lumen can accommodate a threaded cap 198. The threaded cap 198 can be lowered toward the first fastener 106. The threaded cap 198 can couple to the first fastener 106 to retain the rod 112. The threaded cap 198 can couple the rod 112 to the first fastener 106. The threaded cap 198 can exert a force on the rod 112 to seat the rod 112 within the slot 184 of the head 182. The threaded cap 198 can exert a force on the rod 112 which can exert a force on the bulbous surface 186. The threaded cap 198 can exert a force on the rod 112 to prevent or limit the polyaxial movement of the threaded shaft 180.

In some methods, the second fastener 110 is coupled to the second vertebra. The second vertebra can be adjacent to the first vertebra. The second vertebra can be separated from the first vertebra by one or more intermediate vertebra. The second vertebra can be superior to the first vertebra. The second vertebra can be inferior to the first vertebra. The second vertebra can be any vertebra along the spine of the patient. The second fastener 110 can include any feature of the first fastener 106 described herein. The second tower 108 can couple to the second fastener 110. The second tower 108 can be integrally formed with the second fastener 110. The second tower 108 can include any of the features of the first tower 104 described herein. The rod 112 can extend through the slot 194 sized to receive the rod 112 of the second tower 108.

The rod 112 is vertically displaced relative to the head 182 of the second fastener 110. The rod 112 is not seated within the head 182 of the second fastener 110. The rod 112 can be vertically lifted a distance from the desired position within the head 182 of the second fastener 110. The distance can be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, between 5 mm and 20 mm, between 10 mm and 30 mm, at least 5 mm, at least 10 mm, or any range of two of the foregoing values. The rod 112 is within the slot 184 of the head 182 when properly seated. The rod 112 exerts a force on the bulbous surface 186 when properly seated. The rod 112 can be secured by the threaded cap 198 when properly seated. The lever reducer 102 can be utilized to change the position of the second tower 108. The lever reducer 102 can be utilized to change the position of the second fastener 110. The lever reducer 102 can be utilized to change the position of the second vertebra. In some methods, the lever reducer 102 does not change the position of the first tower 104, the first fastener 106, or the first vertebra. In some methods, the lever reducer 102 does not change the position of the rod 112.

In some methods, the rod 112 is not seated within the first fastener 106 before use of the lever reducer 102. The first fastener 106 can be coupled to the first vertebra. The second fastener 110 can be coupled to the second vertebra. If separate components, the first tower 104 can couple to the first fastener 106. If separate components, the second tower 108 can couple to the second fastener 110. The towers 104, 108 can be components of a tower-based screw system. If integrated components, the first fastener 106 and the first tower 104 are coupled to the first vertebra. If integrated components, the second fastener 110 and the second tower 108 are coupled to the second vertebra. The towers 104, 108 can be extended tabs. The towers 104, 108 can be integrated tabs on the fasteners 108, 110. The fasteners 108, 110 and the towers 104, 108 can be minimally invasive pedicle screws with breakoff tabs. The rod 112 is not positioned relative to the first fastener 106 before use of the lever reducer 102. The threaded cap 198 is not positioned relative to the first fastener 106 before use of the lever reducer 102. The rod 112 is not retained relative to the first fastener 106. The lever reducer 102 can be utilized without the rod 112 in position. The lever reducer 102 can lift the second tower 108 relative to the first tower 104. The lever reducer 102 can be utilized prior to introduction of the rod 112. The lever reducer 102 can be used to lift the second tower 108 to align the first tower 104 and the second tower 108 prior to introduction of the rod 112. The lever reducer 102 can be used to lift the head 182 of the second fastener 110. The head of the second fastener 110 and the head of the first fastener 106 can be aligned prior to introduction of the rod 112. The lever reducer 102 can change the vertical displacement of the second fastener 110 to allow introduction of the rod 112 therethrough.

In some methods, the rod 112 can be lowered after use of the lever reducer 102. The rod 112 can be lowered along the first tower 104. The rod 112 can be lowered along the second tower 108. The rod 112 can be lowered along the first tower 104 and the second tower 108 simultaneously. The rod 112 can be seated within the first fastener 106. The rod 112 can be seated within the second fastener 110. The rod 112 can be seated within the first fastener 106 and seated within the second fastener 110 simultaneously. The rod 112 can be seated within the first fastener 106 and seated within the second fastener 110 sequentially. The rod 112 can be seated within the fasteners 106, 110 by lowering the rod 112 along the towers 104, 108. The rod 112 can be seated within the fasteners 106, 110 without lowering the rod 112 along the towers 104, 108. The rod 112 can be introduced after the second tower 108 is vertically lifted.

The rod 112 can be secured to the second fastener 110 while the lever reducer 102 is in use. The threaded cap 198 can secure the rod 112 to the second fastener 110. The lever reducer 102 can be removed. In some methods, the rod 112 can be secured to the first fastener 106 after the lever reducer 102 is removed. The threaded cap 198 can secure the rod 112 to the first fastener 106.

Figure 15C:
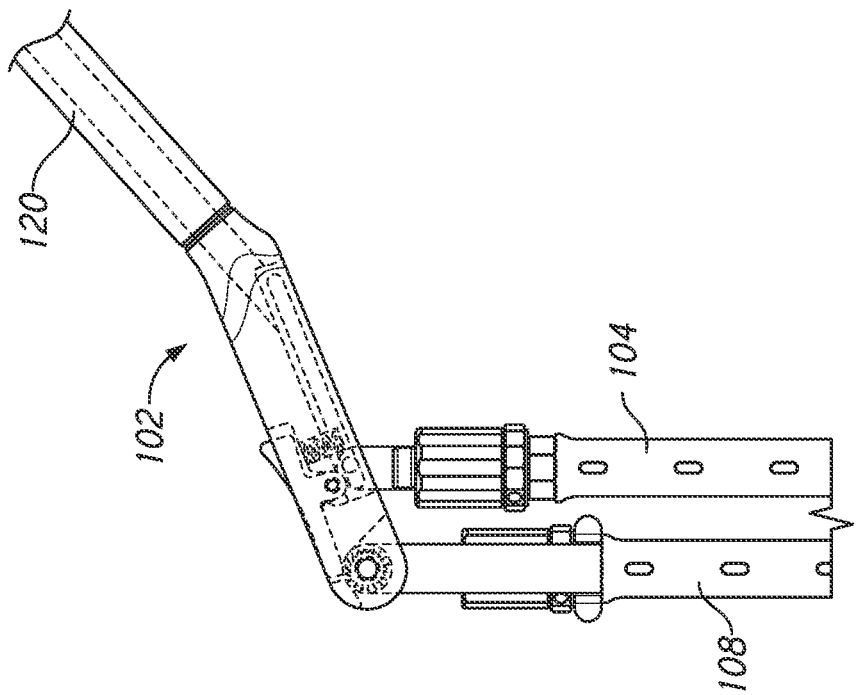

FIGS. 15A-15F illustrate movement of the lever reducer system 100. FIG. 15A illustrates an initial position of the lever reducer system 100 according to some methods. FIGS. 15B-15E illustrate intermediate positions of the lever reducer system 100 as the handle 120 is lowered according to some methods. FIG. 15F illustrates a final position of the lever reducer system 100 according to some methods.

The first fastener 106 is secured to the first vertebra. The second fastener 110 is secured to the second vertebra. The fasteners 106, 110 can be secured in any order. The fasteners 106, 110 can be secured in series or simultaneously. The fasteners 106, 110 can allow for polyaxial movement that accommodates varying anatomical situations. In some methods, the fasteners 106, 110 are coupled to the respective pedicles of the first vertebra and the second vertebra. The first tower 104 can be secured to the first fastener 106 if separate components. The second tower 108 can be secured to the second fastener 110 if separate components. The towers 104, 108 can be secured in any order. The towers 104, 108 can be secured in series or simultaneously. The towers 104, 108 can be secured to the fasteners 106, 110 before securing the fasteners to the vertebrae. The towers 104, 108 can be secured to the fasteners 106, 110 after securing the fasteners to the vertebrae. In some methods, the towers 104, 108 and the fasteners 106, 110 are integrally formed.

The rod 112 can be positioned relative to the slot 194 in the first tower 104. The rod 112 can be positioned relative to the slot 194 in the second tower 108. The rod 112 can be seated within the first fastener 106. The rod 112 can extend to the second tower 108. The threaded cap 198 can be lowered down the first tower 104 to the first fastener 106. The rod 112 can be secured to the first fastener 106. In some methods, the rod 112 is secured to the first fastener 106 before use of the lever reducer 102. In some methods, the threaded cap 198 is secured to the first fastener 106 before use of the lever reducer 102. The rod 112 is coupled to the first fastener 106. The rod 112 extends through the second tower 108. The rod 112 can be vertically offset relative to the second fastener 110 preventing coupling of the rod 112 to the second fastener 110. The rod 112 cannot be secured to the second fastener 110 due to the position of the relative components.

In some methods, the first vertebra is the L5 vertebra. In some methods, the second vertebra is the L4 vertebra. In some methods, the first vertebra is the L4 vertebra. In some methods, the second vertebra is the L5 vertebra, The L5 vertebra is disposed between the L4 vertebra and the sacrum. In some methods, the first vertebra is the S1 vertebra. In some methods, the second vertebra is the L5 vertebra. In some methods, the first vertebra is the L5 vertebra. In some methods, the second vertebra is the S1 vertebra. In some methods, the first vertebra is any sacral vertebra. In some methods, the second vertebra is any other vertebra. In some methods, the first vertebra is any lumbar vertebra. In some methods, the second vertebra is any other lumbar vertebra or any other vertebra. In some methods, the first vertebra is any thoracic vertebra. In some methods, the second vertebra is any other thoracic vertebra or any other vertebra. In some methods, the first vertebra is any cervical vertebra. In some methods, the second vertebra is any other cervical vertebra or any other vertebra. The first vertebra can be any vertebra along the length of the spine. The second vertebra can be any other vertebra along the length of the spine. The first vertebra and the second vertebra can be adjacent. The first vertebra and the second vertebra can be separated by one or more intermediate vertebra.

The towers 104, 108 are coupled to the fasteners 106, 110. Movement of the second tower 108 causes corresponding movement of the second fastener 110. Movement of the second tower 108 causes corresponding movement of the second vertebra. In some methods, the rod 112 can be secured to the first fastener 106 throughout movement of the second tower 108 and the second fastener 110. The rod 112 can be disposed within the second tower 108 throughout movement of the second tower 108 and the second fastener 110. The second tower 108 can slide relative to the rod 112 during movement of the second tower 108 and the second fastener 110. The second fastener 110 can be lifted toward the rod 112 during movement of the second tower 108 and the second fastener 110. In some methods, the rod 112 is not secured to the first fastener 106 during use of the lever reducer 102. The rod 112 can be secured after the second tower 108 is lifted. The rod 112 can be positioned relative to the aligned heads 182 of the fasteners 106, 108 after the second tower 108 is lifted.

The second vertebra can be misaligned relative to the spinal column. The second vertebra can be misaligned due to spondylolisthesis or slippage of the second vertebra. The second vertebra can be slipped relative to a natural curvature. The second vertebra can cause compression of the spinal nerves extending through the foramen. The second vertebra can cause pain due to nerve compression. The second vertebra can have a sagittal deformity. The second vertebra can have a coronal deformity. The second vertebra can have a transverse deformity. The second vertebra can be misaligned relative to the first vertebra due to a deformity or degenerative condition.

The lever reducer 102 can engage the first tower 104. The fulcrum 130 can be at least partially inserted into a lumen of the first tower 104. The fulcrum 130 can be inserted into the tower cap 196 of the first tower 104. In some methods, before the fulcrum 130 is inserted, the threaded cap 198 is inserted into the lumen of the first tower 104. The threaded cap 198 can be rotated to secure the rod 112 to the first fastener 106. The fulcrum 130 can utilize the same lumen as the threaded cap 198.

The lever reducer 102 can engage the second tower 108. The gripping surface 148 can engage the second tower 108. The gripping surface 148 can grip a keyed surface below the tower cap 196 of the second tower 108. The pawl 176 can engage a gear 178. The actuator 144 can be biased by the spring 172. The pawls 176 can be seated in a groove between gears 178. Movement in one direction is allowed by overcoming the biasing force of the spring 172. Movement in the opposite direction is prevented due to the shape of the gears 178. The pawl 176 can maintain a rotational orientation between the towers 104, 108.

The fulcrum 130 can slide within the first engagement feature 132. The first engagement feature 132 can accommodate the relative spacing between the first tower 104 and the second tower 108. The bearing surface 136 of the fulcrum 103 can rest against the tower cap 196. The insertion surface 138 of the fulcrum can be inserted into the first tower 104. The first engagement feature 132 can allow the fulcrum 130 to translate relative to the base 124. The fulcrum 130 can include a pair of pivots 166. The pair of pivots 166 are retained within the side channel 162 as the fulcrum 130 slides in the main translational channel 160. The fulcrum 130 can be at any location along the main translational channel 160. The fulcrum 130 can be at a distal location. The fulcrum 130 can be at a proximal location. The fulcrum 130 can slide to accommodate the spacing between the first tower 104 and the second tower 108. The fulcrum 130 can slide to accommodate the spacing between the first vertebra and the second vertebra. The fulcrum 130 can slide to accommodate the anatomy of the patient. In some embodiments, the fulcrum 130 is a slidable pivot. In some embodiments, the fulcrum 130 is a fixed pivot.

The pair of pivots 166 define the pivot point 200 of the lever reducer 102. The pivot point 200 is movable as the fulcrum 130 moves. The pivot point 200 can slide relative to the base 124. The pivot point 200 can be at any position. The fulcrum 130 can slide based on the orientation of the first tower 104 coupled to the first fastener 106. The polyaxial orientation of the first fastener 106 can be locked when the rod 112 is secured to the first fastener 106. The threaded cap 198 can lock the orientation of the first fastener 106. The first tower 104 can be locked relative to the first fastener 106. The lever reducer 102 can accommodate the fixed relationship between the first vertebra, the first fastener 106, and the first tower 104. The fulcrum 130 can slide to accommodate the fixed orientation of the first tower 104 relative to the first vertebra. In some methods, the first tower 104 is fixed relative to the threaded shaft 180 of the first fastener 106 when the rod 112 is secured. In some methods, the pivot point 200 is movable to limit or prevent applying a force or torque to the threaded shaft 180 of the first fastener 106. The pivot point 200 can be aligned with the first vertebra. In some embodiments, the orientation between the pivot point 200, the first tower 104, the first fastener 106, and the first vertebra can be fixed. In some methods, the base 124 of the lever reducer 102 can translate relative to this pivot point 200. In some methods, the base 124 of the lever reducer 102 can rotate relative to this pivot point 200.

The lever system 100 can include a radial distance 202. The radial distance 202 can be defined between the pivot point 200 and the pin 146. The pin 146 can couple the swivel 140 to the base 124. In some methods, the radial distance 202 is constant during movement of the second tower 108. In some methods, the radial distance 202 defines an arc of movement of the swivel 140. In some methods, the radial distance 202 varies during movement of the second tower 108.

Figure 15D:
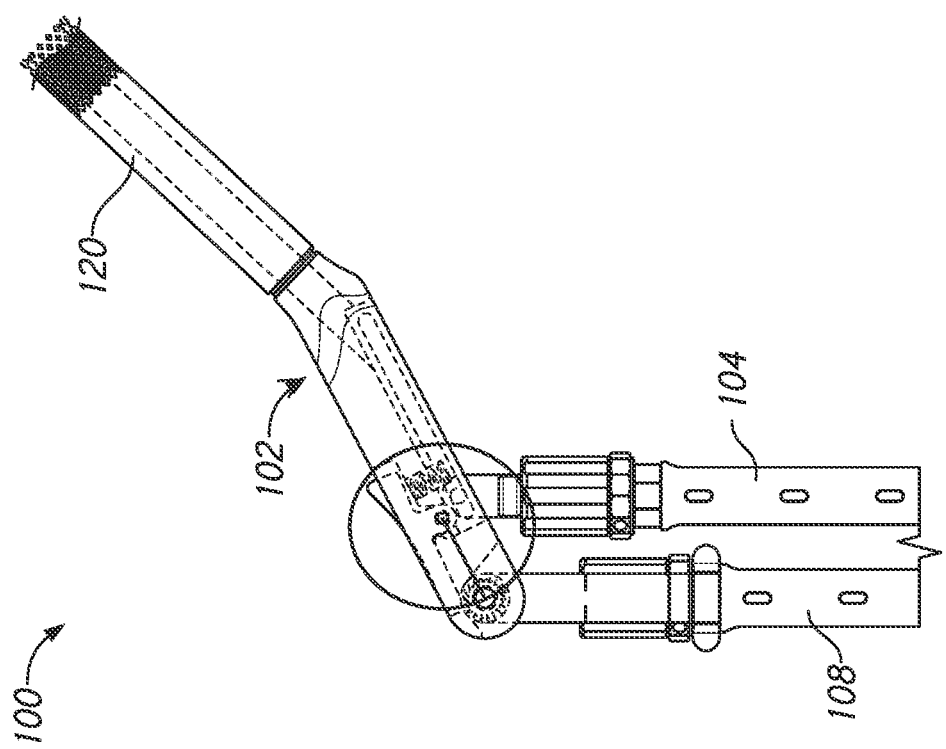

The handle 120 and the base 124 act as a lever relative to the pivot point 200. The user can grip the handle 120. The user can lower the handle 120 as shown in FIGS. 15A-15B. The user can apply a force to the handle 120. The user can apply a downward force. The lever reducer 102 can amplify the input force of the user to a greater output force to lift the vertebra. The lever reducer 102 can provide leverage to facilitate the vertical lift. The lever reducer 102 can lift the swivel 140 coupled to the second vertebra. The swivel 140 can move in an arc relative to the pivot point 200. The swivel 140 can move mostly vertically. The swivel 140 can move slightly outward relative to the first tower 104. The user can continue to lower the handle 120 as shown in FIGS. 15C-15E. The second tower 108 can gradually lift. The second tower 108 can lift relative to the first tower 104.

FIG. 15F illustrates a final position of the second tower 108 according to some methods. In some methods, the first tower 104 and the second tower 108 can have the same height. The second tower 108 can be vertically lifted. In some methods, the first tower 104 and the second tower 108 can have different heights. The second tower 108 can be vertically lifted less than the height of the first tower 104. The second tower 108 can be vertically lifted greater than the height of the first tower 104.

The second tower 108 is gripped by the lever reducer 102 to not obstruct the lumen of the second tower 108. The design allows clearance for an inserter for the threaded cap 198 to be placed in the second tower 108. The second tower 108 is the tower in which rod 112 is being reduced. The threaded cap 198 can be inserted into the second tower 108 and locked to the second fastener 110. The threaded cap 198 can secure the rod 112 to the second fastener 110. The threaded cap 198 can limit or prevent polyaxial movement of the second fastener 110. The threaded cap 198 lock the correction before removing lever reducer 102.

In some methods, a third fastener and a third tower are coupled to the first vertebra. The first fastener 106 and the first tower 104 can be on one side of the first vertebra. The third fastener and the third tower can be coupled to the other side of the first vertebra. In some methods, a fourth fastener and a fourth tower are coupled to the second vertebra. The second fastener 110 and the second tower 108 can be on one side of the second vertebra. The fourth fastener and the fourth tower can be coupled to the other side of the second vertebra. The third tower and the fourth tower can be coupled to the lever reducer 102. In some methods, two lever reducers 102 are utilized to lift the second vertebra. The third fastener and the fourth fastener can have any features of the fasteners described herein. The third tower and the fourth tower can have any features of the towers described herein.

The fasteners 106, 110 can be coupled to the rod 112 to maintain the correction. The lever reducer 102 can be decoupled from the towers 104, 108. The towers 104, 108 can be decoupled from the fasteners 106, 110. In some embodiments, the fasteners 106, 110 and the towers 104, 108 are integrally formed. The towers 104, 108 can be snapped off from the respective fasteners.

The lever reducer system 100 can include several advantages. The lever reducer 102 can easily couple to the towers 104, 108. The lever reducer 102 can include a fulcrum 130 that can be at least partially inserted into the top of the first tower 104. The fulcrum 130 can include a bearing surface 136 that rests against the first tower 104. The fulcrum 130 can include a portion that is inserted into the first tower 104.

The fulcrum 130 defines the pivot point 200 of the lever reducer system 100. The lever reducer 102 pivots relative to the fulcrum 130. The lever reducer 102 pivots relative to the first tower 104. In some methods, the first tower 104 is not raised or lowered. The first tower 104 remains stationary. The first fastener 106 remains stationary. The first vertebra remains stationary. The pivot point 200 is aligned with the first tower 104, the first fastener 106, and the first vertebra.

The fulcrum can include a pair of pivot pins 166 about which the handle 120 and the base 124 pivot. As the handle 120 is lowered, a distal portion of the base 124 is raised. The distal portion of the base 124 can include the swivel 140. The swivel 140 can couple to the second tower 108. The lever reducer 102 pivots relative to the fulcrum 130 to raise the second tower 108. The second tower 108 moves with the distal portion of the base 124 of the lever reducer 102.

The second tower 108 vertically lifts. The second fastener 110 vertically lifts. The second vertebra vertically lifts. The second tower 108 moves in a slight arc relative to the first tower 104. The slight arc can be beneficial for moving the second vertebra relative to the first vertebra. The slight arc can move the second vertebra away from the first vertebra. The slight arc can move the second tower 108 away from the first tower 104. The slight arc can facilitate the alignment of anatomical structures. In some methods, the slight arc can be beneficial over a lift that is only vertical. In some methods, the slight arc can facilitate movement of the second vertebra relative to the first vertebra to avoid or limit interaction between bony prominences on the first vertebra and/or the second vertebra.

The pin 146 of the swivel 140 can define a hinge. The hinge is positioned relative to the fulcrum 130 to allow for mostly vertical lift of a vertebra. The hinge and the fulcrum 130 can be separated by the radial distance 202. The radial distance 202 can be maintained as the second tower 108 lifts. In some embodiments, the radial distance 202 can allow a ratio of lateral displacement to vertical lift. In some embodiments, the lateral displacement is small allowing for mostly vertically lift. In some embodiments, the movement of the swivel 140 along the arc can allow for 1 mm lateral displacement relative to 3 mm vertical lift, 5 mm vertical lift, 7 mm vertical lift, 10 mm vertical lift, 12 mm vertical lift, 15 mm vertical lift, 17 mm vertical lift, 20 mm vertical lift, or 1 mm lateral displacement relative to any range of two of the foregoing values. In some embodiments, the movement of the swivel 140 along the arc can allow for a lateral displacement from 1 mm to 5 mm and a vertical displacement from 3 mm to 30 mm. In some embodiments, the movement of the swivel 140 along the arc can allow for a lateral displacement of 0 mm, 0.5 mm, 1 mm, 1.5 mm, 2 mm, 2.5 mm, 3 mm, 3.5 mm, 4 mm, 4.5 mm, 5 mm, between 1 mm and 2 mm, between 1 mm and 3 mm, between 1 mm and 4 mm, between 1 mm and 5 mm, greater than 1 mm, greater than 2 mm, less than 5 mm, less than 4 mm, or any range of two of the foregoing values. In some embodiments, the movement of the swivel 140 along the arc can allow for a vertical displacement of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, between 5 mm and 10 mm, between 10 mm and 15 mm, between 15 mm and 20 mm, between 20 mm and 25 mm, between 25 mm and 30 mm, between 1 mm and 10 mm, between 10 mm and 20 mm, between 20 mm and 30 mm, or any range of two of the foregoing values.

The fulcrum 130 can translate in the main translational channel 160 within the base 124. The fulcrum 130 can translate to quickly accommodate different spans between towers 104, 108. The fulcrum 130 can translate to quickly accommodate different offsets between vertebral bodies. The fulcrum 130 can translate to allow the lever reducer 102 to be used for patients having different sized vertebra. The fulcrum 130 can translate to allow the lever reducer 102 to be used at any level of the spine. The fulcrum 130 can translate to allow the lever reducer 102 to be used to accommodate a variety of degenerative conditions of the vertebrae.

The second engagement feature 142 maintains correction during the reduction maneuver. The second engagement feature 142 can include a ratchet mechanism with the pawl 176. The pawl 176 engages gears 178. The pawl 176 can be biased in between gears 178 in an initial position of the towers 104, 108. The pawl 176 can allow movement in only one direction. The gears 178 can allow movement in only one direction. The pawl 176 can allow movement of the second tower 108 away from the first tower 104. The pawl 176 can allow the swivel 140 to follow the arc defined by the radial distance 202. The pawl 176 can prevent movement in another direction based on the shape of the gears 178. The pawl 176 can prevent movement of the second tower 108 in a direction opposite to the direction of vertical lift. The pawl 176 can maintain a correction during vertical lift. The pawl 176 can maintain the vertical lift of the second tower 108. The ratchet mechanism can maintain the vertical lift of the second tower 108.

The pawl 176 can maintain a correction if the lever reducer 102 is at one or more intermediate positions. The pawl 176 can be biased by the spring 172 acting on the lever arm 170. The force of the spring 172 can facilitate maintaining the correction at one or more intermediate positions. The force of the spring 172 can facilitate maintaining the correction if force is no longer applied to the handle 120.

In some methods, the lever reducer system 100 can be designed to lock the rod 112 to the first fastener 106 before engagement of the lever reducer 102. In some methods, the lever reducer system 100 can be designed to lock the rod 112 to the first fastener 106 after removal of the lever reducer 102. The first tower 104 can be aligned with the pivot point 200 during operation of the lever reducer 102. The first fastener 106 and the first tower 104 can be aligned with the pivot point 200 during operation of the lever reducer 102. Once the second fastener 110 and the second tower 108 are vertically lifted, the lever reducer 102 allows the threaded cap 198 to be inserted into the second tower 108 to secure the rod 112 to the second fastener 110. In some methods, the rod 112 can be secured to the fasteners 106, 110 before removing the lever reducer 102 from the towers 104, 108. In some methods, the rod 112 can be secured to the first fastener 106 before utilizing the lever reducer 102. In some methods, the rod 112 can be secured to the second fastener 110 during use of the lever reducer 102. In some methods, the rod 112 can be secured to the first fastener 106 after utilizing the lever reducer 102.

While certain embodiments have been shown and described herein, it will be clear to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

What is claimed is:

1. A lever reducer system comprising:
a first tower comprising a longitudinal axis;
a second tower; and
a lever reducer configured to couple to the first tower and the second tower, wherein the lever reducer comprises a handle, wherein the lever reducer comprises a fulcrum configured to be coupled to the first tower by lowering the fulcrum at least partially into the first tower along the longitudinal axis, wherein the lever reducer comprises a swivel configured to be coupled to the second tower, wherein the handle is on a first side of the fulcrum and the swivel is on a second side of the fulcrum, wherein the lever reducer is configured to pivot the lever reducer about the fulcrum to vertically lift the second tower while the first tower remains stationary when a force is applied to the handle, wherein the swivel comprises a pin that defines a hinge, wherein the hinge and the fulcrum are separated by a distance that is maintained as the second tower lifts such that the motion of the second tower is mostly vertical.

2. The lever reducer system of claim 1, wherein the fulcrum is configured to be at least partially inserted into a lumen of the first tower through which a threaded cap was inserted.

3. The lever reducer system of claim 1, wherein the fulcrum is configured to translate relative to a base of the lever reducer.

4. The lever reducer system of claim 1, wherein the fulcrum is configured to rotate relative to a base of the lever reducer.

5. The lever reducer system of claim 1, wherein the fulcrum comprises a slidable pivot.

6. The lever reducer system of claim 1, wherein the fulcrum is configured to translate in a channel within a base of the lever reducer to accommodate different spans between the first tower and the second tower.

7. The lever reducer system of claim 1, wherein the fulcrum is configured to translate into one or more locking grooves that provide discrete translational positions.

8. The lever reducer system of claim 1, wherein the swivel is configured to rotate in one direction, but rotation in the opposite direction is limited or prevented.

9. The lever reducer system of claim 1, further comprising a ratchet mechanism that maintains the vertical lift of the second tower.

10. The lever reducer system of claim 1, wherein a lumen of the second tower is accessible during vertical lift of the second tower.

11. The lever reducer system of claim 1, wherein the first tower comprises a lumen extending an entire length of the first tower along the longitudinal axis.

12. The lever reducer system of claim 1, wherein the second tower comprises a lumen extending an entire length of the second tower, wherein the lumen of the second tower is accessible during vertical lift of the second tower.

13. The lever reducer system of claim 1, wherein the swivel comprises a keyed socket configured to be inserted around the second tower.

14. The lever reducer system of claim 1, wherein the second tower comprise a keyed surface configured to engage the swivel.

15. A method of using a lever reducer system comprising:
coupling a first tower to a first vertebra, wherein the first tower comprises a longitudinal axis;
coupling a second tower to a second vertebra;
coupling a lever reducer to the first tower and the second tower by coupling a fulcrum of the lever reducer to the first tower by lowering the fulcrum at least partially into the first tower along the longitudinal axis and coupling a swivel of the lever reducer to the second tower, wherein the lever reducer comprises a handle, wherein the handle is on a first side of the fulcrum and the swivel is on a second side of the fulcrum, wherein the swivel comprises a pin that defines a hinge; and
applying a force to the handle of the lever reducer to pivot the lever reducer about the fulcrum to vertically lift the second tower while the first tower remains stationary, wherein the hinge and the fulcrum are separated by a distance that is maintained as the second tower lifts such that the motion of the second tower is mostly vertical.

16. The method of claim 15, wherein the first vertebra and the second vertebra are lumbar vertebrae.

17. The method of claim 15, further comprising translating the fulcrum within a channel of a base of the lever reducer to accommodate different spans between the first tower and the second tower.

18. The method of claim 15, further comprising translating the fulcrum within a channel of a base of the lever reducer to accommodate different offsets between the first vertebra and the second vertebra.

19. The method of claim 15, further comprising translating the fulcrum into one or more locking grooves that provide discrete translational positions.

20. The method of claim 15, further comprising engaging a pawl with a gear to maintain the vertical lift of the second tower.

21. The method of claim 15, further comprising securing a rod to a fastener while the lever reducer is coupled to the first tower and the second tower.

22. The method of claim 15, further comprising securing a rod to a fastener before coupling the lever reducer to the first tower and the second tower.

* * * * *